(12) United States Patent
Mayer

(10) Patent No.: US 8,187,333 B2
(45) Date of Patent: May 29, 2012

(54) INTERVERTEBRAL DISC PROSTHESIS AND METHOD FOR IMPLANTING AND EXPLANTING

(76) Inventor: Peter L. Mayer, Sarasota, FL (US)

( * ) Notice: Subject to any disclaimer, the term of this patent is extended or adjusted under 35 U.S.C. 154(b) by 743 days.

(21) Appl. No.: 12/233,107

(22) Filed: Sep. 18, 2008

(65) Prior Publication Data
US 2010/0070035 A1    Mar. 18, 2010

(51) Int. Cl.
*A61F 2/44* (2006.01)
(52) U.S. Cl. .................................................. 623/17.16
(58) Field of Classification Search ................ 606/246, 606/300–331; 623/17.11–17.16
See application file for complete search history.

(56) References Cited

U.S. PATENT DOCUMENTS

| | | | |
|---|---|---|---|
| 2,485,531 A * | 10/1949 | Dzus et al. ................. | 606/310 |
| 4,041,939 A * | 8/1977 | Hall .......................... | 606/254 |
| 4,349,921 A | 9/1982 | Kuntz | |
| 4,772,287 A | 9/1988 | Ray et al. | |
| 4,944,753 A | 7/1990 | Burgess | |
| 5,047,055 A | 9/1991 | Bao et al. | |
| 5,100,405 A * | 3/1992 | McLaren .................... | 606/304 |
| 5,298,254 A | 3/1994 | Prewett | |
| 5,514,180 A | 5/1996 | Heggeness | |
| 5,545,229 A | 8/1996 | Parsons et al. | |
| 5,562,735 A * | 10/1996 | Margulies .................. | 601/61 |
| 5,662,657 A * | 9/1997 | Carn ......................... | 606/95 |
| 5,865,846 A | 2/1999 | Bryan | |
| 5,951,553 A * | 9/1999 | Betz et al. ................. | 606/279 |
| 5,964,807 A | 10/1999 | Chin Chin Gan | |
| 6,048,342 A * | 4/2000 | Zucherman et al. ........ | 606/249 |
| 6,063,121 A | 5/2000 | Xavier et al. | |
| 6,093,205 A | 7/2000 | McLeod et al. | |
| 6,110,210 A | 8/2000 | Norton et al. | |
| 6,126,688 A | 10/2000 | McDonnell | |
| 6,146,420 A * | 11/2000 | McKay ...................... | 623/17.16 |

(Continued)

FOREIGN PATENT DOCUMENTS
DE        4208116        9/1993
(Continued)

OTHER PUBLICATIONS

International Preliminary Report on Patentability and Written Opinion dated Mar. 22, 2011 for PCT/US2009/057369 filed Sep. 17, 2009.

(Continued)

*Primary Examiner* — Eduardo C Robert
*Assistant Examiner* — Steven Cotroneo
(74) *Attorney, Agent, or Firm* — Fleit Gibbons Gutman Bongini & Bianco, PL; Martin Fleit; Paul D. Bianco

(57) ABSTRACT

Prosthesis for inserting into a damaged intervertebral disc having an elongated tubular main prosthesis body with a length to fit laterally from one side of a disc to the other at its mid-plane. The main prosthesis body has a vertical height slightly greater than the height of normal disc space of the damaged intervertebral disc into which it is to be implanted, and a shape in cross section normal to its longitudinal axis so that main prosthesis body makes appropriate contact with vertebrae abutting to the damaged intervertebral disc. Heads having a vertical height greater than the vertical height of the main prosthesis body are mounted on the ends of the main prosthesis body. A method for implanting from one side only and a method for explanting from one side only.

23 Claims, 13 Drawing Sheets

U.S. PATENT DOCUMENTS

| | | | |
|---|---|---|---|
| 6,146,422 A | 11/2000 | Lawson | |
| 6,214,012 B1 * | 4/2001 | Karpman et al. | 606/93 |
| 6,240,926 B1 | 6/2001 | Chin Chin Gan | |
| 6,264,695 B1 | 7/2001 | Stoy | |
| 6,287,308 B1 * | 9/2001 | Betz et al. | 606/263 |
| 6,368,319 B1 * | 4/2002 | Schaefer | 606/60 |
| 6,419,704 B1 | 7/2002 | Ferree | |
| 6,419,706 B1 | 7/2002 | Graf | |
| 6,451,020 B1 | 9/2002 | Zucherman et al. | |
| 6,494,883 B1 | 12/2002 | Ferree | |
| 6,500,178 B2 | 12/2002 | Zucherman et al. | |
| 6,500,206 B1 | 12/2002 | Bryan | |
| 6,733,531 B1 | 5/2004 | Trieu | |
| 6,929,640 B1 | 8/2005 | Underwood | |
| 6,966,930 B2 | 11/2005 | Arini et al. | |
| 6,974,479 B2 | 12/2005 | Trien | |
| 6,997,929 B2 | 2/2006 | Manzi | |
| 7,001,431 B2 | 2/2006 | Bao et al. | |
| 7,004,971 B2 | 2/2006 | Serhan et al. | |
| 7,048,764 B2 | 5/2006 | Ferree | |
| 7,101,400 B2 | 9/2006 | Thramann | |
| 7,153,305 B2 | 12/2006 | Johnson | |
| 7,204,853 B2 | 4/2007 | Gordon | |
| 7,238,206 B2 | 7/2007 | Lange | |
| 7,250,060 B2 | 7/2007 | Trieu | |
| 7,261,738 B2 | 8/2007 | Casey | |
| 7,270,682 B2 | 9/2007 | Frigg et al. | |
| 7,371,238 B2 | 5/2008 | Soboleski | |
| 2002/0120334 A1 * | 8/2002 | Crozet | 623/17.11 |
| 2002/0183848 A1 | 12/2002 | Ray et al. | |
| 2003/0176921 A1 | 9/2003 | Lawson | |
| 2003/0204260 A1 | 10/2003 | Ferree | |
| 2004/0010317 A1 | 1/2004 | Lambrechi et al. | |
| 2004/0097927 A1 * | 5/2004 | Yeung et al. | 606/61 |
| 2004/0258732 A1 | 12/2004 | Shikinami | |
| 2005/0015150 A1 | 1/2005 | Lee | |
| 2005/0015152 A1 | 1/2005 | Sweeney | |
| 2005/0113919 A1 | 5/2005 | Cragg et al. | |
| 2005/0113923 A1 | 5/2005 | Acker et al. | |
| 2005/0182414 A1 | 8/2005 | Manzi | |
| 2005/0187559 A1 | 8/2005 | Raymond | |
| 2006/0136061 A1 | 6/2006 | Navarro et al. | |
| 2006/0161166 A1 | 7/2006 | Johnson | |
| 2006/0235534 A1 | 10/2006 | Gertzman et al. | |
| 2006/0253132 A1 * | 11/2006 | Evans et al. | 606/151 |
| 2006/0253198 A1 | 11/2006 | Myint et al. | |
| 2006/0276897 A1 | 12/2006 | Winslow et al. | |
| 2006/0276901 A1 | 12/2006 | Zipnick et al. | |
| 2006/0276902 A1 | 12/2006 | Zipnick et al. | |
| 2006/0287730 A1 | 12/2006 | Segal et al. | |
| 2007/0010889 A1 | 1/2007 | Francis | |
| 2007/0027546 A1 | 2/2007 | Palm et al. | |
| 2007/0038222 A1 | 2/2007 | Bhatnagar et al. | |
| 2007/0038301 A1 | 2/2007 | Hudgins | |
| 2007/0050037 A1 | 3/2007 | Snell et al. | |
| 2007/0061012 A1 | 3/2007 | Cauthen, III | |
| 2007/0067039 A1 | 3/2007 | Lambrecbt et al. | |
| 2007/0073402 A1 | 3/2007 | Vresilovic et al. | |
| 2007/0179612 A1 | 8/2007 | Johnson | |
| 2007/0239280 A1 | 10/2007 | Keith | |

FOREIGN PATENT DOCUMENTS

| | | |
|---|---|---|
| EP | 0042271 | 12/1981 |
| FR | 2639823 | 6/1990 |
| FR | 2723841 | 3/1996 |
| FR | 2772594 | 6/1999 |
| FR | 2862866 | 6/2005 |
| WO | 0013620 | 3/2000 |
| WO | 0013691 | 3/2000 |
| WO | 2004064692 | 8/2004 |
| WO | 2004089240 | 10/2004 |
| WO | 2005084589 | 9/2005 |
| WO | 2006078663 | 7/2006 |
| WO | 2007048252 | 5/2007 |

OTHER PUBLICATIONS

International Search Report dated May 4, 2010 for PCT/US2009/057369 filed Sep. 17, 2009.

* cited by examiner

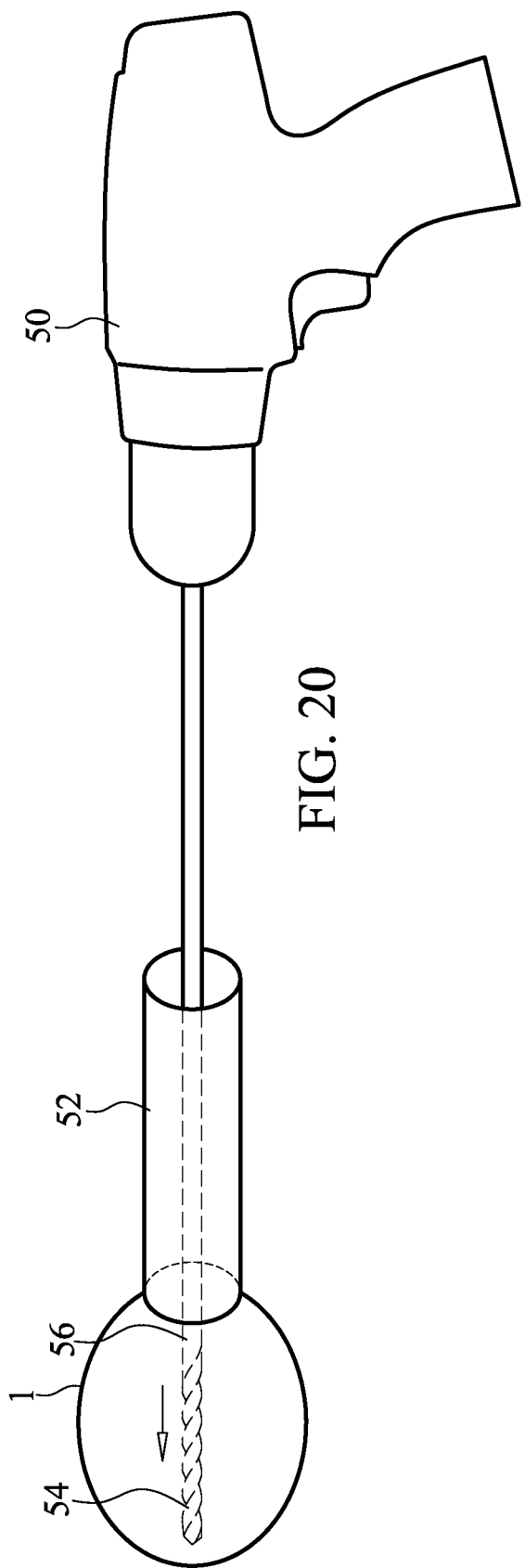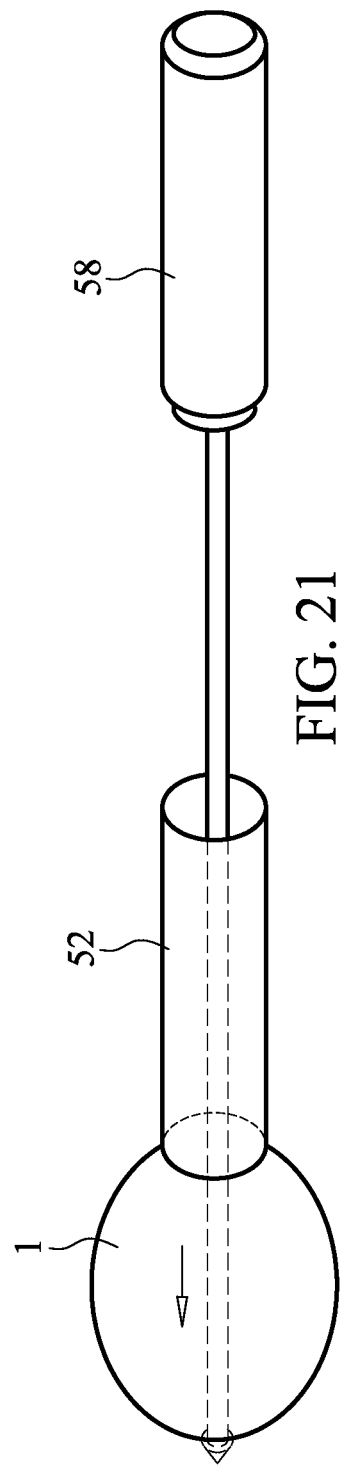
FIG. 20
FIG. 21

INTERVERTEBRAL DISC PROSTHESIS AND METHOD FOR IMPLANTING AND EXPLANTING

BACKGROUND OF THE INVENTION

1. Field of the Invention

The invention relates to prostheses for intervertebral discs that are easily and quickly implantable, a method for easily and quickly implanting and a method for easily and quickly explanting.

2. Description of the Related Art

Intervertebral discs (or more simply "discs") lie between adjacent vertebrae in the spine. Each disc forms a cartilaginous joint to allow slight movement of the vertebrae and acts as a ligament to hold the vertebrae together.

Discs include an outer annulus fibrosus, which surrounds the inner nucleus pulposus. The annulus fibrosus includes several layers of fibrocartilage. The nucleus pulposus contains loose fibers suspended in a mucoprotein gel, which has the consistency of semi-hard and slightly fibrous connective tissue or cartilage. The nucleus of the disc acts as a shock absorber for distributing pressure evenly across the disc and for absorbing the impact of bending and twisting of the spine while keeping the two abutting vertebrae separated. When one develops a prolapsed disc, the nucleus pulposus is forced out resulting in pressure being put on nerves located near the disc. This can cause severe pain and neurological problems.

There is one disc between each pair of adjacent vertebrae, except between the first and second cervical vertebrae. The atlas is the first cervical (neck) vertebra which is just under the head. The axis is the second cervical vertebra. The axis acts as a post around which the atlas can rotate, allowing the neck to rotate. There are a total of twenty-three discs in the spine. The discs are most commonly identified by specifying the particular vertebrae they separate. For example, the disc between the fifth and sixth cervical vertebrae is designated "C5-6".

As people age, the intervertebral discs degenerate. Two typical processes occur. The nucleus pulposus dehydrates and flattens, which limits its ability to absorb shock. The annulus fibrosus gets weaker with age and develops fissures or tears. As the discs dehydrate, the disc spaces change and the space for adjacent nerves narrows. In the neural foramens, this is called foraminal stenosis; in the spinal canal, this is called central stenosis. The discs bulge outward, and bone spurs (osteophytes) form along the bulging disc surfaces that also pinch adjacent nerves (spinal cord, cauda equina, and nerve roots). A flattening disc causes stress to the posterior elements of the spine and also the facet joints. Although these conditions may not cause pain in some people, others experience acute and chronic pain.

Pain, weakness, and numbness due to pinching of the nerves protruding from the spine are called radiculopathy or radiculitis. Pain, weakness, and numbness due to pinching of the nerves inside the spinal canal is known as radiculopathy, radiculitis, cauda equina syndrome or myelopathy, depending on the level of the spine and the type of symptoms.

When the annulus fibrosus tears due to an injury or the degenerative process, the nucleus pulposus can begin to extrude through the tear. This is called disc herniation. Near the posterior aspect of each disc, at each vertebral level or segment, a pair of major spinal nerves extends outward, to different organs, tissues, extremities, etc. Herniated discs often press against these nerves (pinched nerve) and the spinal cord causing neurologic dysfunction including sensory and/or motor loss and/or pain.

Herniated disc, ruptured disc, bulging disc, degenerative disc, protrusion, extrusion, all refer to related processes and are used more-or-less synonymously, depending on the medical professional. There is no true standard nomenclature, and the various terms mean different things to different people. Also, the degree to which there is pressure on the nerves (e.g. stenosis, pinching, nerve root elevation, cord compression, effacement, and many other descriptions) also varies.

To treat impaired discs, many techniques and devices have been used. Some treatments remove, dissolve, or vaporize disc material (e.g. chymopapain injection, microsurgical discectomy, nucleotomy, laser discectomy, radiofrequency ablation, and others). Other treatments fuse the disc (e.g. cages, screws, bone grafts, bone morphogenic protein, and others). Disc removal procedures remove the disc. Fusion procedures result in loss of motion of the disc and juxtaposed vertebrae.

Accordingly, there is a need for an implantable prosthesis that treats the conditions noted above in a more efficacious manner to restore to a damaged disc area the original natural body motion function. This need is met by the implantable prosthesis of the invention that is easily and quickly implantable. Using the prosthesis of the present invention, adjacent and abutting vertebrae adjacent to the damaged disc area will be able to move relative to each other in a more natural way. The prosthesis of the invention enables motion of the adjacent and abutting vertebrae the same as the natural motion of healthy adjacent vertebrae of the spine. In particular, the prosthesis that can be easily and quickly positioned relative to a normal axis of rotation, and will function to support or restore normal vertebral movement. The prosthesis of the invention is implanted into a damaged intervertebral disc in a simple and direct manner. The prosthesis of the invention affords "dynamic stabilization" and "motion preservation.

SUMMARY OF THE INVENTION

It is accordingly an object of the invention to provide a novel intervertebral disc prosthesis that is quickly and easily implantable, a method for quickly and easily implanting and a method for quickly and easily explanting the novel intervertebral disc prosthesis in the event the indications are such that removal of the prosthesis is desirable. The prosthesis of the present invention overcomes the above-mentioned disadvantages of known prosthesis of this general type. The foregoing object of the invention is accomplished by the novel disc prosthesis of the present invention, which consists of an elongated metal, ceramic or hard plastic, biocompatible implant that has a shape suitable for insertion into the nucleus pulposus of a degenerative intervertebral disc to restore normal body motion with respect to the adjacent and abutting vertebrae. The implant is placed through the disc annulus laterally and extends from one side to the other and has caps or heads on its ends that bear against the adjacent vertebrae, so that it is held in position. It is not meant for fusion, but rather is meant to allow for natural or near natural motion of the spine. When implanted, the disc prosthesis has a height slightly greater than the normal disc spatial opening and thus, slightly distracts the adjacent and abutting vertebrae. It can be used for cervical, thoracic or lumbar degenerative discs.

In accordance with the invention, in its preferred form, the novel prosthesis is assembled from three members, namely, (i) an elongated main prosthesis body of a preselected shape having a height or vertical thickness greater than the normal disc height, and having at one end a proximal cap (integrally formed or attached) having a height greater than the body height, (ii) a distal cap having a height greater than the body height is mounted on the other end of the main prosthesis body and (iii) a locking member coacting with the other two members that prevents rotary motion and holds the assembly together. The prosthesis can include quickly attachable and detachable acting mutually coacting elements to lock the prosthesis axially to prevent disassembly except when desired. The assembled novel prosthesis is implanted laterally from one side (the proximal side) into a hole drilled into the disc space and spans the intervertebral disc space completely from side-to-side so that the distal and proximal caps contact opposed lateral sides of the disc and the adjacent, abutting vertebrae. As the height of the main prosthesis body is greater than the normal disc height, when implanted, the abutting vertebrae are slightly distracted and placed under slight tension. The main prosthesis body has a length at least as great as the disc lateral width. To implant, an annulotomy track or annulotomy hole is drilled laterally through the disc in the region of its central vertical plane using minimally invasive surgical techniques, such as, arthroscopic techniques, i.e. the hole is drilled from one side of the disc only laterally to the other side. The final section of the hole is completed by a punch to create a lateral through hole. Using a suitable instrument, the assembled prosthesis is quickly and easily forced through the hole from the proximal side of the disc laterally to the distal side of the disc. During this process, the distal cap distracts significantly the adjacent, abutting vertebrae. When the distal cap has passed through and emerges out the distal lateral side, the adjacent, abutting vertebrae retract slightly to contact the main prosthesis body. However, because the height of the main body of the prosthesis is greater than the height of the disc space, the adjacent, abutting vertebrae are still slightly distracted and under slight tension. Due to the shape of the main prosthesis body, the contact between the main prosthesis body and the adjacent, abutting vertebrae is a line or point contact, or an areal contact that is very narrow in a direction normal to the longitudinal axis of the prosthesis and the distal and proximal caps slightly contact opposed lateral sides of the disc and the adjacent, abutting vertebrae enabling a rotation of the implant about its longitudinal axis. To quickly and easily explant the prosthesis, special tools are used to first unlock the prosthesis by removal of the locking member, then to remove the distal cap from the main prosthesis body, and finally to pull the main prosthesis body out from the proximal side of the lateral hole in the disc. The distal head, now separate from the rest of the implant, remains in the body.

The prosthesis can take other forms, such as, it may consist of a single rod or tube with integral or detachable heads, or only one head is detachable. The rod or two can be in two parts that are connected together axially, by, for example, by threading, or splines, or any other connecting elements that hold the two parts together. The prosthesis can take a form that does or does not include the locking member described above.

To begin an implant procedure, a tube is inserted or a working channel is created using a lateral approach to the disc at its lateral mid-plane. A skin incision is made to only one side of the intervertebral disc, i.e. the prosthesis is placed from one side of the patient's body only. The tube or cannula is placed against the lateral side of the intervertebral disc in which the prosthesis is to be inserted. The tube provides a working space in which the prosthesis and tools are delivered to the intervertebral disc. A minimally-invasive technique may be accomplished in a known manner, such as with a tube retractor. A drill is initially delivered via the tube or working channel to drill a guide track and a nearly through hole in the intervertebral disc. This procedure is known as an annulotomy. The annulotomy defines a track laterally through the intervertebral disc. The final opening on the distal side of the disc is made using a punch or awl. Now the lateral through hole is completed and has a proximal opening and a distal opening. The location of the lateral hole is at its lateral mid-plane or just posterior to this point, the slightly more posterior location being close to the natural axis of rotation of the spinal segment. Preferably, the location is from a location near the lateral mid-plane of the disc to a location at a parallel plane not more than one-half the distance from the lateral mid-plane of the disc to the posterior of the disc.

The next step of the method involves forcing the assembled prosthesis distal cap first into and through the hole along the annulotomy track from the proximal side of the disc to the distal side of the disc whereupon it emerges. This is quickly and easily accomplished. As noted, because the distal cap is of a greater height than the prosthesis body and the disc, the adjacent, abutting vertebrae are distracted during this step. With the prosthesis fully implanted, both the distal and proximal caps lie outside the disc and bear laterally against the proximal and distal sides of the disc and also bear against the adjacent, abutting vertebrae.

The present invention discloses a prosthesis for inserting into an intervertebral disc having a normal disc height, a normal disc width, and a disc annular wall, comprising:

i. an elongated tubular main prosthesis body having opposed ends having a length to fit laterally from one side of a disc to the other at its mid-plane, said main prosthesis body having a vertical height slightly greater than the height of normal disc space of an intervertebral disc into which it is to be inserted, and having a shape in cross section normal to its longitudinal axis so that main prosthesis body makes contact with abutting vertebrae to the intervertebral disc parallel with its longitudinal axis in one of a line, a point and an area, which has a very narrow width normal to the longitudinal axis of the main prosthesis body;

ii. a first head mounted on one end of the main prosthesis body having a vertical height greater than the vertical height of the main prosthesis body; and iii. a second head mounted on the other end of the main prosthesis body having a vertical height greater than the vertical height of the main prosthesis body.

The prosthesis can have one head detachably mounted on the main prosthesis body. The prosthesis can further include a locking member to prevent relative movement of at least one head and the main prosthesis body.

The novel prosthesis for inserting into an intervertebral disc has a disc height, a disc width, and a disc annular wall can comprise:

i. an elongated tubular main prosthesis body having opposed ends, having a longitudinally extending through passageway open at its ends and having a length to fit laterally from one side of a disc to the other at its mid-plane, said main prosthesis body having a vertical height slightly greater than the height of normal disc space of an intervertebral disc into which it is inserted, and having a shape in cross section normal to its longitudinal axis so that main prosthesis body makes contact with abutting vertebrae to the intervertebral disc parallel with its longitudinal axis in one of a line, a point and an area, which has a very narrow width normal to the longitudinal axis of the main prosthesis body;

ii. a first head attached to one end of the main prosthesis body having a vertical height greater than the vertical height of the main prosthesis body and defining an opening in alignment with one end of said passageway;

iii. a second head detachably attached to the other end of the main prosthesis body having a vertical height greater than the vertical height of the main prosthesis body and defining a opening in alignment with the other end of said passageway; and iv. a locking member received in said passageway having a first element engaging the opening in said first head and a second element engaging the opening of said second head to prevent relative detachment.

The prosthesis as noted above can have its main prosthesis body cylindrical in shape, and the main prosthesis body can be one of right cylindrical, elliptical and prolate spheroid in shape. The main prosthesis body can be made from a material selected from the group consisting of metal, a synthetic polymer, rubber, ceramic, PEEK, acrylic, and combinations thereof. The heads can be disc shaped. The second or distal head can be attached to the main prosthesis body by a joint that requires relative rotation to detach. The openings in the heads can be non-circular shaped. The opening in the second or distal head can be hex shaped. The locking member can have a hex shaped end that fit into the hex opening in the second or distal head.

The locking member of the prosthesis and the second or distal head can have quick detachable mutually coacting elements that prevent longitudinal movement of the locking member relative to the second head. The quick detachable mutually coacting elements can comprise projecting flat bars peripherally arranged in a hex shape at the end of the locking member, each bar having peripherally extending bump coacting with a shoulder defined in the hex opening of the second or distal member. The first and second heads can have flat surfaces facing inwardly toward the main prosthesis body that can bear against the annular wall and the abutting vertebrae when the prosthesis is implanted in the disc, but without too much pressure so that relative rotation is not impeded. The opening in said first or proximal head can be hex shaped and the locking member can have a hex shaped end that fits into the hex opening of the first head in a recessed manner. The hex shaped openings and the coacting hex shaped elements can have other shapes, such as, square, diamond, cruciform, triangular, octagonal or any other non-circular shape.

An aspect of the present invention is a method for treating a person having a damaged intervertebral disc comprising the steps of:

i. providing a prosthesis comprised of (a) an elongated tubular main prosthesis body having opposed ends having a length to fit laterally from one side of a disc to the other at its mid-plane, said main prosthesis body having a vertical height slightly greater than the height of normal disc space of a damaged intervertebral disc into which it is implanted, and having a shape in cross section normal to its longitudinal axis so that main prosthesis body makes contact with abutting vertebrae to the damaged intervertebral disc parallel with its longitudinal axis in one of a line, a point and an area, which has a very narrow width normal to the longitudinal axis of the main prosthesis body, (b) a first head mounted on one end of the main prosthesis body having a vertical height greater than the vertical height of the main prosthesis body (c) a second head mounted on the other end of the main prosthesis body having a vertical height greater than the vertical height of the main prosthesis body;

ii. forming a hole laterally completely through the damaged intervertebral disc to create opening in the intervertebral disc on opposed lateral sides, iii. feeding the prosthesis into the hole in the damaged intervertebral disc from one side only; and iv. then forcing the prosthesis through the hole in the damaged intervertebral disc so that the heads project out of said openings on both sides of said damaged intervertebral disc; wherein the projecting heads bear against the vertebrae abutting to the damaged intervertebral disc.

In another aspect the invention is a method for treating a person having a damaged intervertebral disc comprising the steps of:

i. providing a prosthesis comprised of (a) an elongated tubular main prosthesis body having opposed ends, having a longitudinally extending through passageway open at its ends and having a length to fit laterally from one side of a disc to the other at its mid-plane, said main prosthesis body having a vertical height slightly greater than the height of normal disc space of an intervertebral disc into which it is inserted, and having a shape in cross section normal to its longitudinal axis so that main prosthesis body makes contact with abutting vertebrae to the intervertebral disc parallel with its longitudinal axis in one of a line, a point and an area, which has a very narrow width normal to the longitudinal axis of the main prosthesis body, (b) a first head attached to one end of the main prosthesis body having a vertical height greater than the vertical height of the main prosthesis body and defining an opening in alignment with one end of said passageway, (c) a second head detachably attached to the other end of the main prosthesis body having a vertical height greater than the vertical height of the main prosthesis body and defining a opening in alignment with the other end of said passageway and (d) a locking member received in said passageway having a first element engaging the opening in said first head and a second element engaging the opening of said second head to prevent relative detachment;

ii. forming a hole laterally completely through the damaged intervertebral disc to create openings on opposed lateral sides of the damaged intervertebral disc, iii. feeding the prosthesis into the hole in the damaged intervertebral disc from one side only; and iv. then forcing the prosthesis through the hole in the damaged intervertebral disc so that the heads project out of said openings on both sides of said damaged intervertebral disc; wherein the projecting heads bear against vertebrae abutting to the damaged intervertebral disc.

In a still further aspect the invention is a method for treating a person having a damaged intervertebral disc between abutting vertebrae comprising the steps of:

a. providing a prosthesis comprised of (i) an elongated main prosthesis body having opposed ends, having a length to fit laterally from one side of a disc to the other, said main prosthesis body having a vertical height slightly greater than the height of normal disc space of an intervertebral disc into which it is inserted, and having a shape in cross section normal to its longitudinal axis so that main prosthesis body makes contact with abutting vertebrae to the intervertebral disc parallel with its longitudinal axis, said body containing bone material exposed to grow to vertebral surfaces; and (ii) a head attached to each end of the main prosthesis body having a vertical height greater than the vertical height of the main prosthesis body;

b. forming a hole laterally completely through the damaged intervertebral disc to create openings on opposed lateral sides of the damaged intervertebral disc, c. feeding the prosthesis into the hole in the damaged intervertebral disc from one side only; and d. then forcing the prosthesis through the hole in the damaged intervertebral disc so that the heads project out of said openings on both sides of said damaged intervertebral disc;

wherein the main prosthesis body lies between the abutting vertebrae distracting them slightly so that the exposed bone material contacts the surfaces of the abutting vertebrae and the projecting heads bear against the abutting vertebrae.

In yet another aspect the invention is a method for treating a person having a damaged intervertebral disc comprising the steps of:

a. providing a prosthesis comprised of (i) an elongated tubular main prosthesis body having opposed ends having a length to fit laterally from one side of a disc to the other at its mid-plane, said main prosthesis body having a vertical height slightly greater than the height of normal disc space of a damaged intervertebral disc into which it is implanted, and having a shape in cross section normal to its longitudinal axis so that main prosthesis body makes contact with abutting vertebrae to the damaged intervertebral disc parallel with its longitudinal axis, and the main prosthesis body having an hollow annular configuration with an outer surface being one of flexible and resilient, said main prosthesis body being one of fillable by a liquid and inflatable by a gas, (ii) a first head mounted on one end of the main prosthesis body having a vertical height greater than the vertical height of the main prosthesis body, (iii) a second head mounted on the other end of the main prosthesis body having a vertical height greater than the vertical height of the main prosthesis body;
b. forming a hole laterally completely through the damaged intervertebral disc to create opening in the intervertebral disc on opposed lateral sides,
c. feeding the prosthesis into the hole in the damaged intervertebral disc from one side only; and
d. then forcing the prosthesis through the hole in the damaged intervertebral disc so that the heads project out of said openings on both sides of said damaged intervertebral disc;

wherein the projecting heads bear against the vertebrae abutting to the damaged intervertebral disc.

The invention also contemplates a method of explanting a prosthesis implanted according to the above including the steps of:

e. engaging the implanted prosthesis from a proximal side;
f. detaching the distal head of the prosthesis from the proximal side; and
g. removing the remaining portion of the implanted prosthesis from the proximal side.

In another embodiment, a method of explanting can include the steps of:

e. engaging the implanted prosthesis from a proximal side;
f. unlocking and removing the locking member from the proximal side;
g. detaching the distal head of the prosthesis from the proximal side; and
h. removing the unlocked remaining portion of the implanted prosthesis from the proximal side.

Other features and advantages of the invention will be evident from the following detailed description when taken in conjunction with the appended drawings. Changes may be made therein, as will be evident to those of skill in the art, without departing from the spirit, scope and teachings herein of the invention and its range of equivalents as expressed in the claims.

BRIEF DESCRIPTION OF THE DRAWING

FIGS. 20 and 21 are diagrammatic views showing the drilling of a lateral hole in a disc, and completing the lateral hole in a disc by means of a punch or awl, respectively.

DETAILED DESCRIPTION OF PREFERRED EMBODIMENTS OF THE INVENTION

Figure 2:
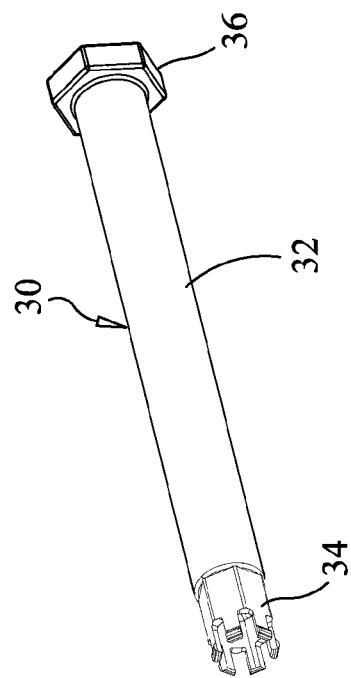
FIG. 2 is an exploded view showing the three members of a first embodiment of a novel prosthesis of the present invention disc
Figure 2:
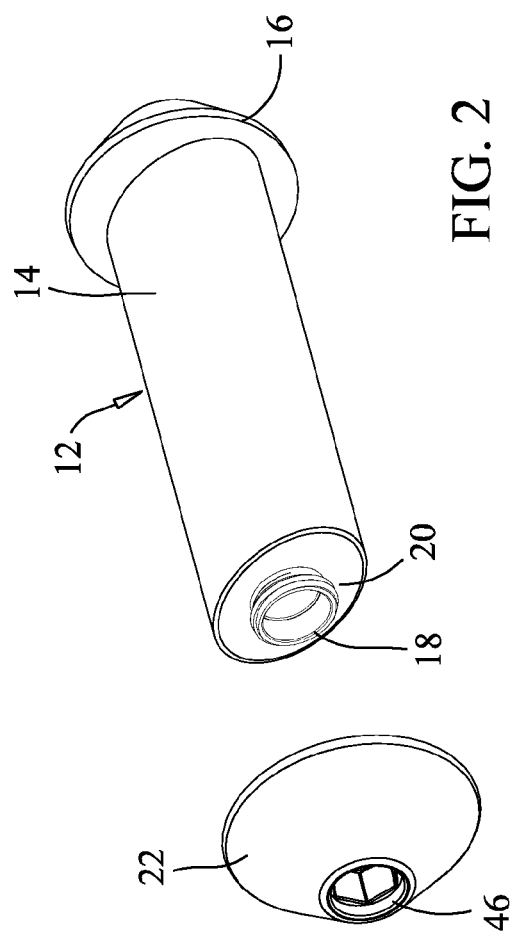
Figure 3:
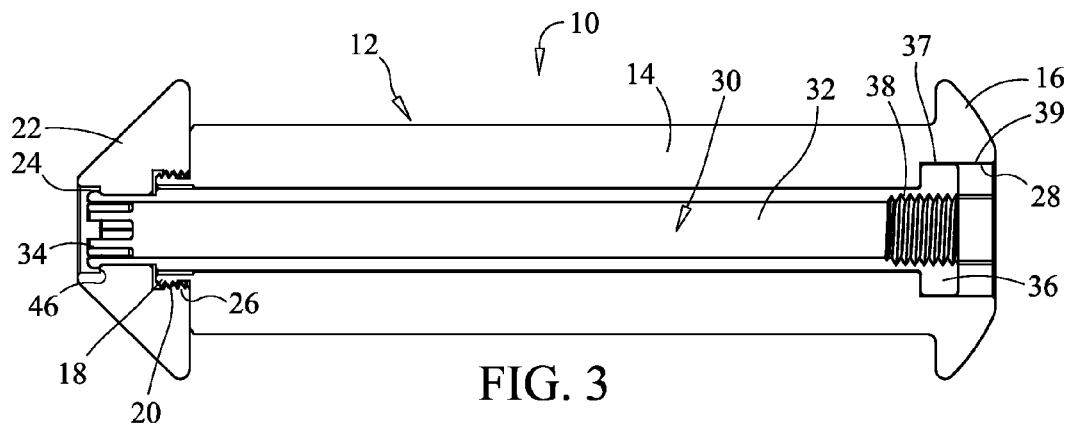
FIG. 3 is a cross sectional view showing the details of a second embodiment of the prosthesis.
Figure 4:
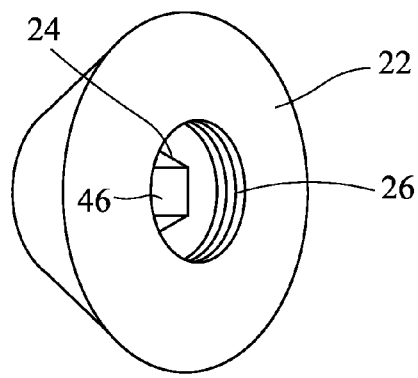
FIG. 4 is a perspective view of a distal cap.
Figure 7:
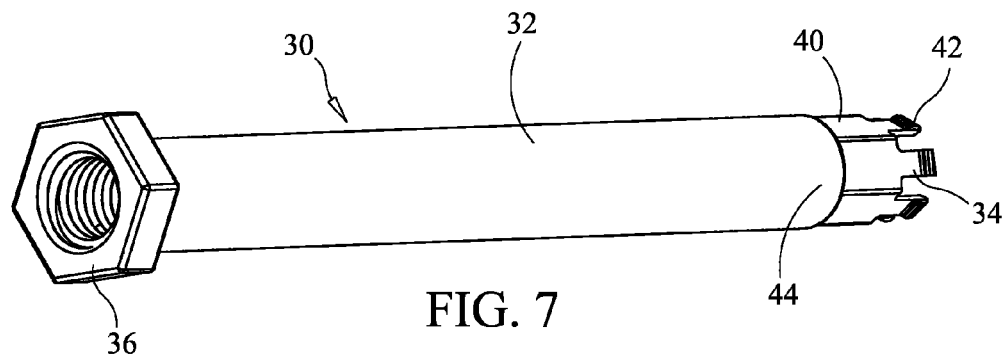
FIG. 7 is a perspective view of a second type locking member.

Referring now to the figures of the drawing in detail and first, particularly to FIGS. 1 to 7 and 18 to 21, the prosthesis of the present invention will be described structurally first and then the method of implanting laterally in an intervertebral disc 1. As shown in FIG. 3, for example, the prosthesis 10 consists of (i) a main prosthesis body 12 in the form of an elongated cylindrical tube 14 having a cap 16 with a recessed hex opening 28 integrally formed at one end and a reduced section 18 at its other end formed with a thread 20, (ii) a cap 22 formed with a recessed hex opening 24 (smaller in diameter than recess hex opening 28) on its side facing outwardly and a recessed threaded section 26 on its side facing inwardly for attachment to the threaded reduced section 18, and (iii) a hex locking member 30 in the form of an elongated tube or rod 32 having at one end a hex form 34 that fits into and mates with the hex opening 24 of cap 22, and at its other end an enlarged hex flange or head 36 that fits into and mates with the inner portion of the recessed hex opening 28 of the cap 22 and with the internal surface of the tube 32 having threads 38 extending from the hex flange 36 inwardly for a preselected length axially along the internal surface of tube 32. The hex locking member 30 takes two forms, the form of FIG. 6 as described above, which prevents relative rotary motion between the hex locking member and the main prosthesis body, or the form of FIG. 7, which prevents relative rotary and axial motion between the hex locking member and the main prosthesis body. The two forms differ at the end that coacts with the cap 22. As shown in FIG. 7, the hex form at this end of hex locking member 30 is made of six projecting, peripherally spaced, axial extending, cantilever-projecting flat bars or fingers 40 arranged in a hex configuration with each bar 40 having a transverse rounded projection 42 at its terminal end 44 for cooperating with a recessed shoulder 46 formed in the hex opening 24 of the cap 22. In this manner the rounded projections 42 engage shoulder 46 to provide an axial locking action preventing the axial movement of the hex locking member 30 relative to the cap 22 and the main body of the prosthesis 12. The projections and the shoulder 46 constitute quickly attachable and detachable acting mutually coacting elements to lock the prosthesis axially to prevent disassembly except when desired. Rotary locking action is provided by the hex configurations at both ends of the hex locking member 30 mating with hex openings 24 and 28. The assembled prosthesis is shown in section in FIG. 3 with the hex locking member taking the form of FIG. 7. When the hex locking member takes the form of FIG. 6, an axial locking action is provided by, for example, a ball detent located in the hex opening 28 coacting with a recess formed in the hex flange 36. In this case, the ball detent and recess constitute quickly attachable and detachable acting mutually coacting elements to lock the prosthesis axially to prevent disassembly except when desired. Rotary or radial locking action is provided on at one end of the prosthesis by the mating of the hex configuration at the end of the member 30 with the hex opening 24 in cap 22 and on the other end of the prosthesis by the mating of the hex flange 36 mating with the inner portion 37 of the hex opening 28 of the cap 16. The outer portion 39 of the hex opening 28 is reserved for explant tools. Other assembled prostheses are shown in FIGS. 8, 10, 12, 14, 15, 18, 22, 23, 24 and 27.

Figure 1:
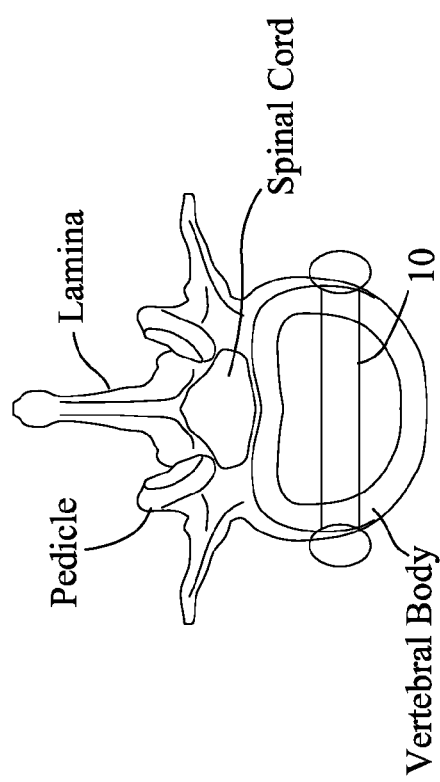
FIG. 1 is a diagrammatic view of the novel prosthesis of the present invention implanted into a disc.
Figure 19:
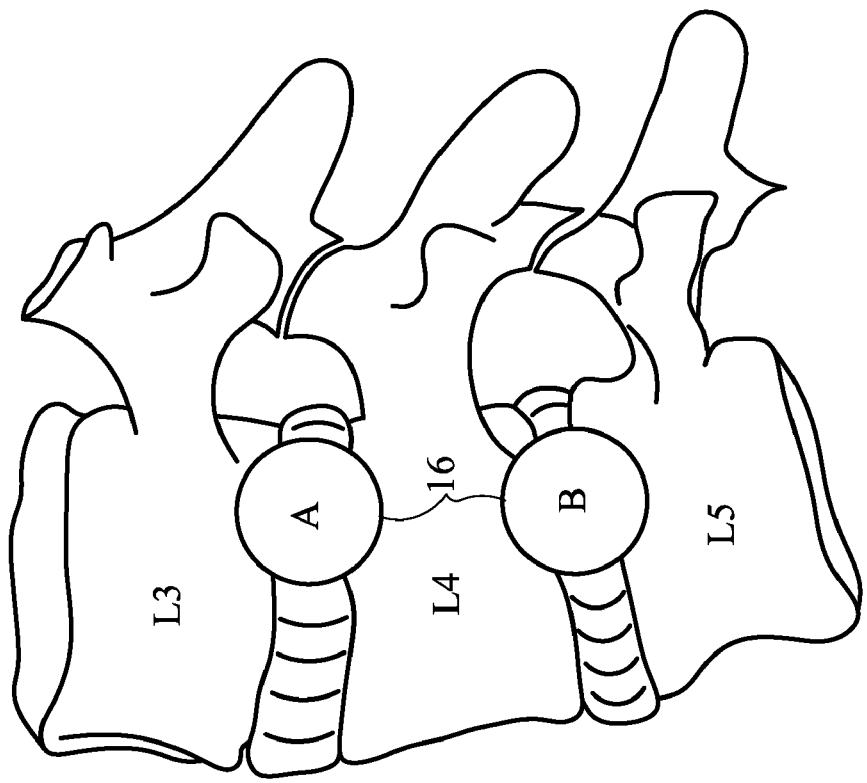
FIG. 19 is a side view of FIG. 18.
Figure 18:
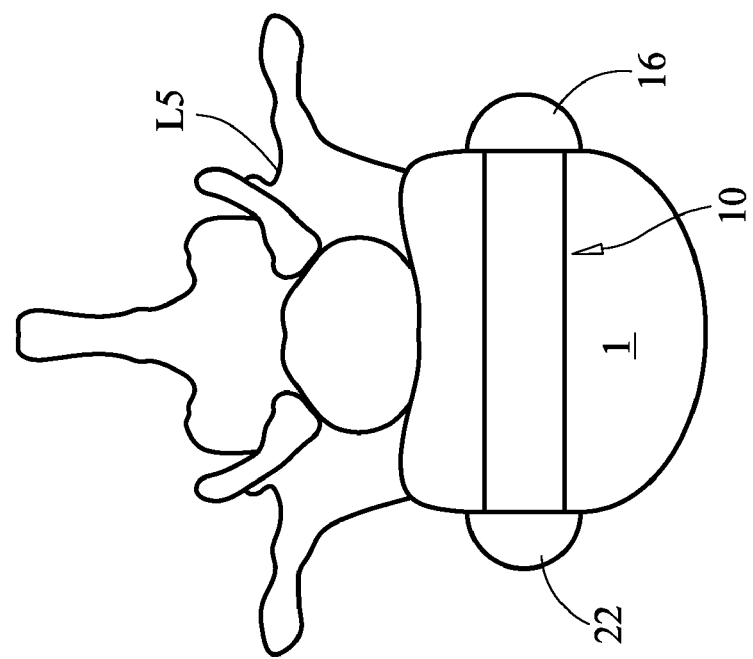
FIG. 18 is a diagrammatic view showing implanting of prosthesis of the present invention into a disc.

The prosthesis 10, in assembled form, as shown for example in FIG. 3, is implanted laterally into a vertebral disc 1 as shown in FIGS. 1 and 18 with the caps 16 and 22 extending to the outside of the disc 1 on both sides. As the caps 16 and 22 are of greater height relative to the prosthesis body 14, which in turn is of greater height relative to the disc space, the outer edges of the caps 16 and 22 extend vertically sufficiently to bear against the adjacent, abutting vertebrae L3, L4 and L5, as shown in FIG. 19. The principal object of the prosthesis is to restore to a damaged disc area the original natural body motion function regarding the abutting and interconnected vertebrae. To this end, the assembled novel prosthesis 10 is implanted laterally, from one side only, into a hole drilled laterally through the disc space and spans the intervertebral disc space completely, so that the distal and proximal caps contact opposed (both proximal and distal) lateral sides of the disc and the abutting vertebrae. The height of the main prosthesis body is greater than the normal disc height, when implanted, and thus, the adjacent and abutting vertebrae are slightly distracted and placed under slight tension. The main prosthesis body has a length at least as great as the disc lateral width. To implant, as shown in FIG. 20, an annulotomy track or annulotomy hole is drilled laterally through the disc in the region of its central vertical plane using minimally invasive surgical techniques, such as, laparoscopic techniques. Drill 50 is introduced through a cannula 52 to one side (proximally) of the disc 1. The drill bit 54 bores a hole 56 in disc 1. An awl 58 punches the hole through the annulus of the disc 1. The hole 56 is drilled only from one side (proximal) of the disc laterally to the other side (distal). The final section of the hole is completed by a punch or awl 58 to create a lateral through hole, as shown in FIG. 21.

To begin an implant procedure, a tube 52 is inserted or a working channel is created using a lateral approach to the disc 1 at its lateral vertical mid-plane. The terms proximal and distal reference to how the prosthesis is inserted into the intervertebral disc 1. A skin incision is made to only one side of the intervertebral disc 1. The prosthesis 10 is placed from one side of the patient's body only. The tube or cannula 52 is placed in a known manner against the lateral side of the intervertebral disc 1 in which the prosthesis 10 is to be inserted. The tube 52 provides in a well known manner a working space in which the prosthesis 10 and tools are delivered to the intervertebral disc 1. A minimally-invasive technique may be accomplished with a tube retractor. A drill 50 is initially delivered via the tube or working channel 52 to drill a guide track and nearly through hole in the intervertebral disc 1. This procedure is known as an annulotomy. The annulotomy defines a track 56 laterally through the intervertebral disc 1. The final opening on the distal side of the disc is made using a punch 58. Now the lateral through hole 56 is completed and has a proximal opening and a distal opening.

The next step of the method involves quickly and easily forcing the assembled prosthesis distal cap 22 first into and through the hole 56 along the annulotomy track from the proximal side of the disc 1 to the distal side of the disc 1 whereupon it emerges. As noted, as the distal cap is of a greater height than the body 14 of the prosthesis and the disc 1. Accordingly, the adjacent, abutting vertebrae are significantly distracted during this step. With the prosthesis fully implanted, both the distal and proximal caps 22 and 16 are outside the disc 1 bearing laterally against the distal and proximal sides of the disc 1 and also bearing against the adjacent, abutting vertebrae. By a suitable instrument, the assembled prosthesis 10 is forced quickly and easily through the hole 56 from the proximal side of the disc 1 laterally to the distal side of the disc 1. During this process, the distal cap 22 distracts the adjacent, abutting vertebrae. When the distal cap 22 has passed through and emerged out the distal lateral side, the vertebrae retract slightly to contact the main prosthesis body 14. As the main body 14 of the prosthesis 10 is slightly greater in height than the normal disc space, the adjacent, abutting vertebrae are still slightly distracted and under slight tension. To explant the prosthesis 10, special tools are used to first quickly and easily to pull the hex locking member 30, and then, special tools are used to quickly and easily remove or detach the distal cap 22 and pull out the main prosthesis body 12. All this activity takes place quickly and easily from the proximal side of the lateral hole in the disc 1. Explanting will be described in detail hereinafter.

Figure 5:
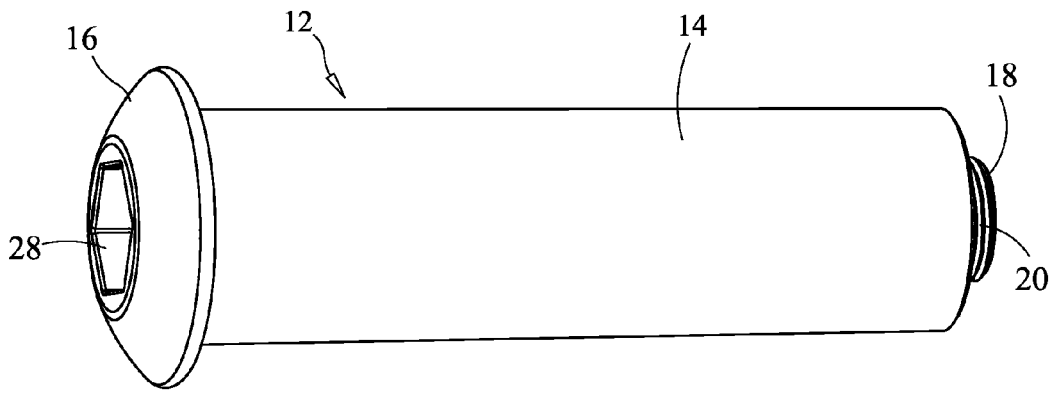
FIG. 5 is a perspective view of the main prosthesis body of the second embodiment.
Figure 6:
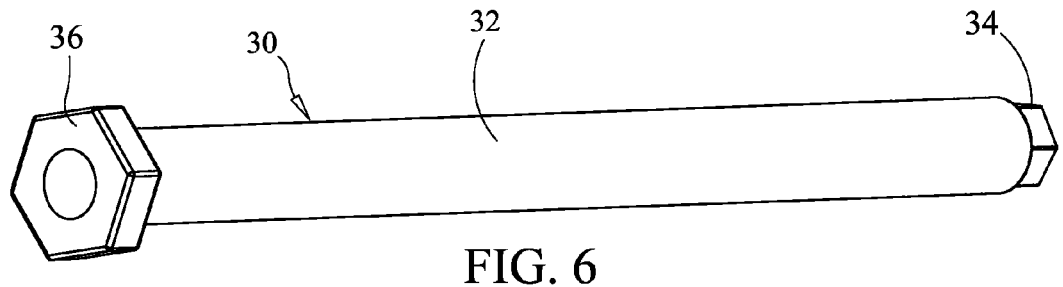
FIG. 6 is a perspective view of a first type locking member.
Figure 8:
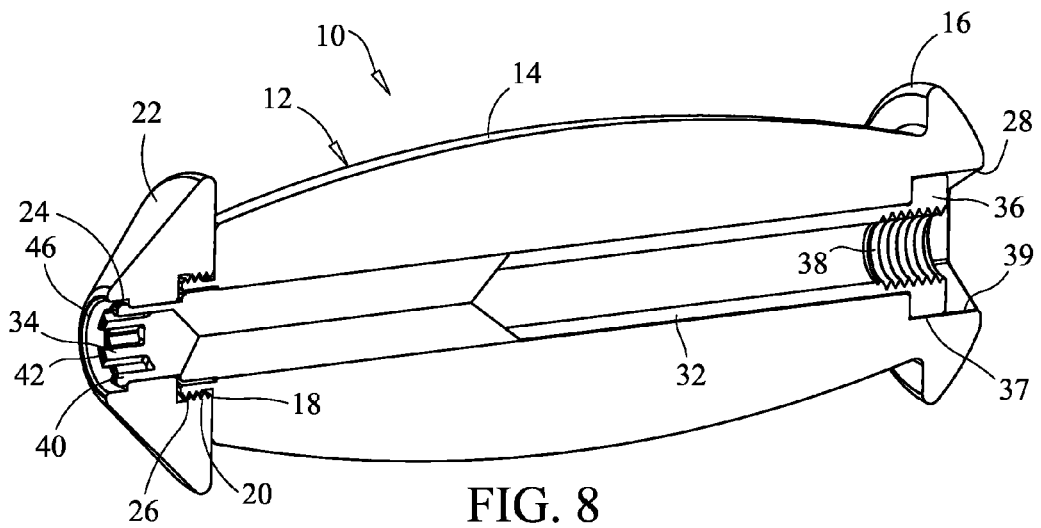
FIG. 8 is a cross sectional view showing the details of a third embodiment of the prosthesis.

Due to the shape of the main prosthesis body, the contact between the main prosthesis body and the abutting vertebrae surfaces is a line or point contact or an areal contact of very narrow width in a direction normal to the longitudinal axis of the prosthesis 10. The width of the areal contact is limited so that the prosthesis will not restrict normal motion of the adjacent, abutting vertebrae. The shape of the main prosthesis body 12 is preferably cylindrical having a cross section of one of a circle or an ellipse. An elliptical shape is shown in FIG. 2 for example; a right cylindrical shape is shown in FIG. 5 for example; a prolate spheroid shape is shown in FIG. 8 for example. The shape of the main prosthesis body 14 can assume other configurations so long as the contact between the prosthesis 10 and the vertebral surfaces is essentially line or point contact or areal contact having a very small width normal to the longitudinal axis of the prosthesis.

Figure 9:
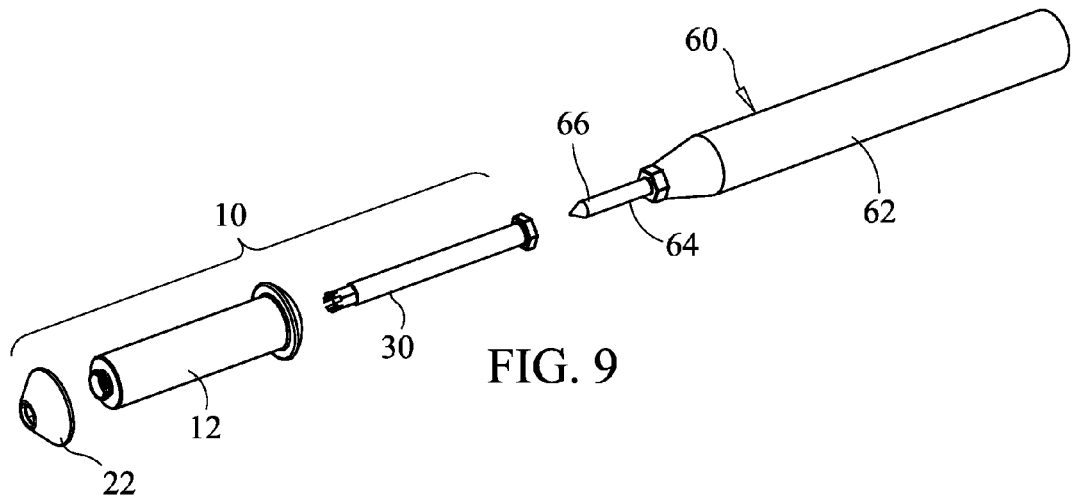
FIG. 9 is an exploded view showing the insertion tool for implanting a prosthesis.

A suitable implant tool 60 is shown in FIG. 9 and consists of a elongated handle 62 terminating on one end with a threaded shaft portion, screw or bolt portion 64 that has matching threads 66 to the threads 38 cut into the inner surface of the hex locking member 30. However, bolt portion 64 can be without threads, if desired, as the function of implant tool 60 is only to push the prosthesis into and through the hole in the disc. This can be done by simply inserting the unthreaded bolt into the bore of the locking member 30 and pushing the prosthesis through the hole drilled in the damaged disc. As shown in FIG. 9, prosthesis 10 according to the invention consisting of a cap 22, a main body 12 of right cylindrical shape and a hex locking member 30 is preassembled as previously described, and then, the portion 64 is threaded into the hex locking member 30. The implant 10 is then forced quickly and easily into and through the prepared lateral hole 56 in the disc 1 from the proximal side into the juxtaposition as shown in FIGS. 1 and 18-19, whereupon the implant tool 60 is unthreaded and removed. Due to the end caps 16 and 22 the prosthesis seats itself quickly and easily in the disc space. The dimensioning of the prosthesis relative to the disc hole is that the main prosthesis body, when seated and in place, distracts the abutting vertebrae slightly and the two heads 16 and 22 bear against the abutting vertebrae, but do not prevent or unduly impede the relative rotation of the distal head 22 and the main prosthesis body during explanting a will be described in detail hereinafter.

To implant, explained in more detail, the procedure is accomplished using the following steps:
1. Length and diameter of implant 10 is chosen pre-operatively based on CT or MRI scan measurements.
2. Tube retractor 52 goes in place against lateral aspect of disc.
3. Annulotomy drilled through disc under biplanar fluoroscopic guidance.
4. Far end punctured with awl 58.
5. Track 56 is dilated under fluoroscopy with trial implant (not shown). This confirms length and diameter of implant 10.
6. Preassembled implant 10 (including internal hex locking member 30 in place) is loaded onto the insertion tool 60 (FIG. 9) on back table.
7. Whole assembly is placed through the tube retractor 52 against the lateral proximal side of the disc 1 at the annulotomy hole 56.
8. Mallet is used to tap implant 10 into place under fluoroscopic guidance.
9. Proximal cap or head 16 stops implant 10 when fully inserted.
10. Implant tool is removed.
11. Final AP and lateral films confirm placement of prosthesis.

Figure 10:
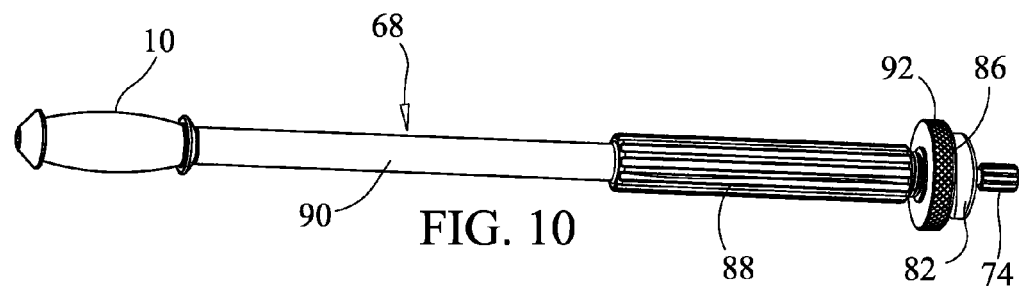
FIG. 10 is a perspective view showing a first type removal tool attached to a third embodiment of the prosthesis.
Figure 11:
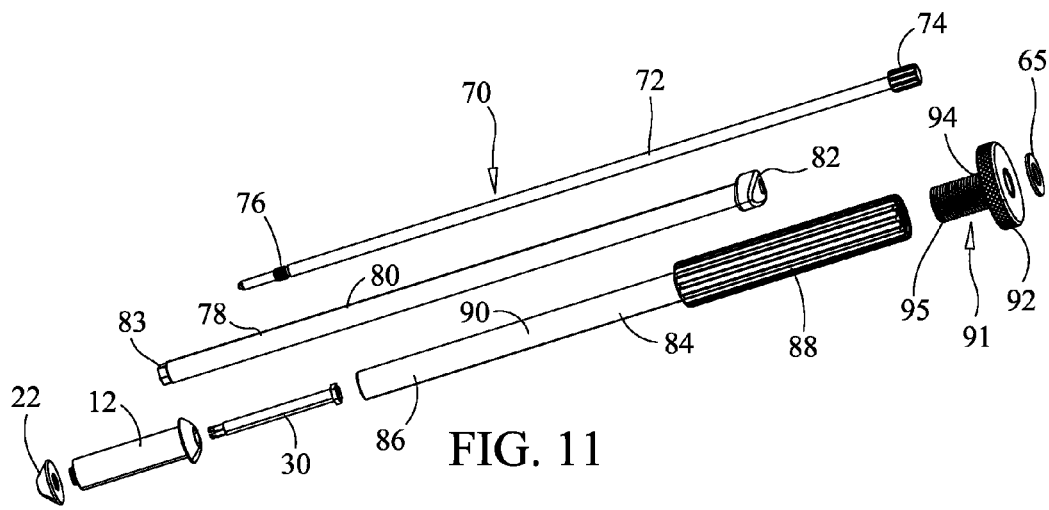
FIG. 11 is an exploded view of the first type removal tool of FIG. 10 with an exploded view of the second embodiment of the prosthesis.
Figure 12:
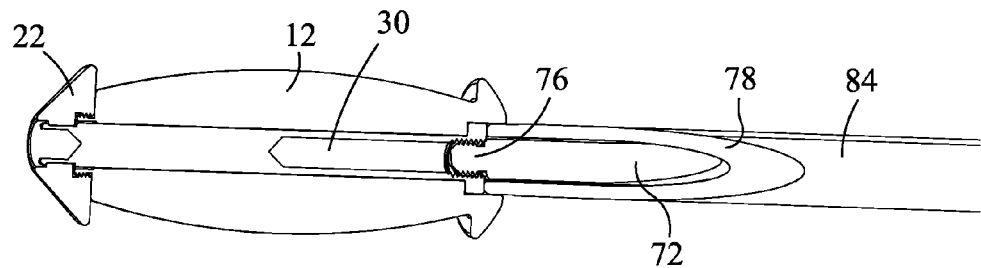
FIG. 12 is a detail view partly cutaway of the removal tool of FIG. 10 attached to a cutaway of the third embodiment of the prosthesis.
Figure 13:
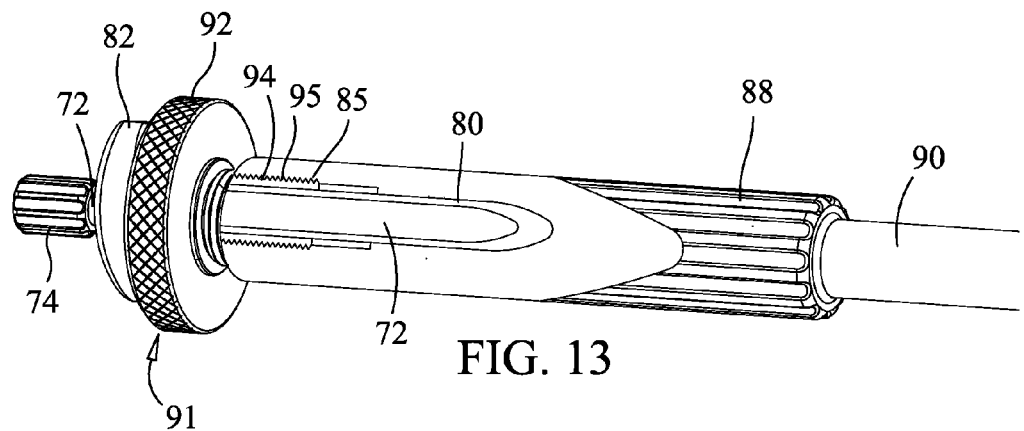
FIG. 13 is another detail view partly cutaway of the removal tool of FIG. 10.

To explant quickly and easily a prosthesis, two tool are required, one for removing the hex locking member 30 and one to detach the cap 22 and remove the main prosthesis body 12. FIGS. 10 to 13 show a first embodiment of a removal tool 68 for removing the hex locking member 30. As shown, the tool consists of an elongated lock removal tool 70 having a rod or shaft 72, a knurled head 74 at one end of shaft 72 and a threaded screw 76 at its other end; a removal hex tool 78 having an open tubular shaft 80 with a non-circular head 82 at one end and a hex shape 83 at its other end, a lock removal sheath 84 having an open tube 86 with an enlarged section 88 threaded on the inside and a reduced section 90; an insert removal tool 91 consisting of a peripherally knurled knob 92 with a depending open cylinder 94 fixed to the knob 92 at one end, the outer surface of the cylinder 94 being threaded at 95 to mate with the threads 85 on the inside of sheath 84; and a nylon washer 65. To assemble, the insert removal tool 91 is threaded into the tubular sheath 84. The removal hex tool 78 is passed through the insert removal tool 91 and the sheath 84. The tool 70 is received in tubular removal hex tool 78 with the knurled head projecting and with the nylon washer 65 between the non-circular head 82 and the knob 92. The assembled removal tool is shown in FIG. 10.

The preassembled tool assembly is placed down the tube retractor 52 and engaged into the hex opening on the implant 10 with the sheath 84 bearing on the cap 16 and the hex shape 83 inserted into the hex opening 28. The threaded end 76 of rod 70 is screwed (clockwise) into the hex locking member 30 of the prosthesis 10 to be removed. The surgeon's left hand holds handhold sheath 84 while his/her right hand screws knob 92 clockwise. Threads 85 on inside of 84 mating with threads 95 on the cylinder 94 are reverse. This forces outwardly the knob 92 (and hex tool 78 and tool 70), disengaging the hex locking member 30 from the distal head 22 of the implant 10. The whole assembly of the removal tool can now be pulled all the way out bringing with it the hex locking member 30.

Figure 16:
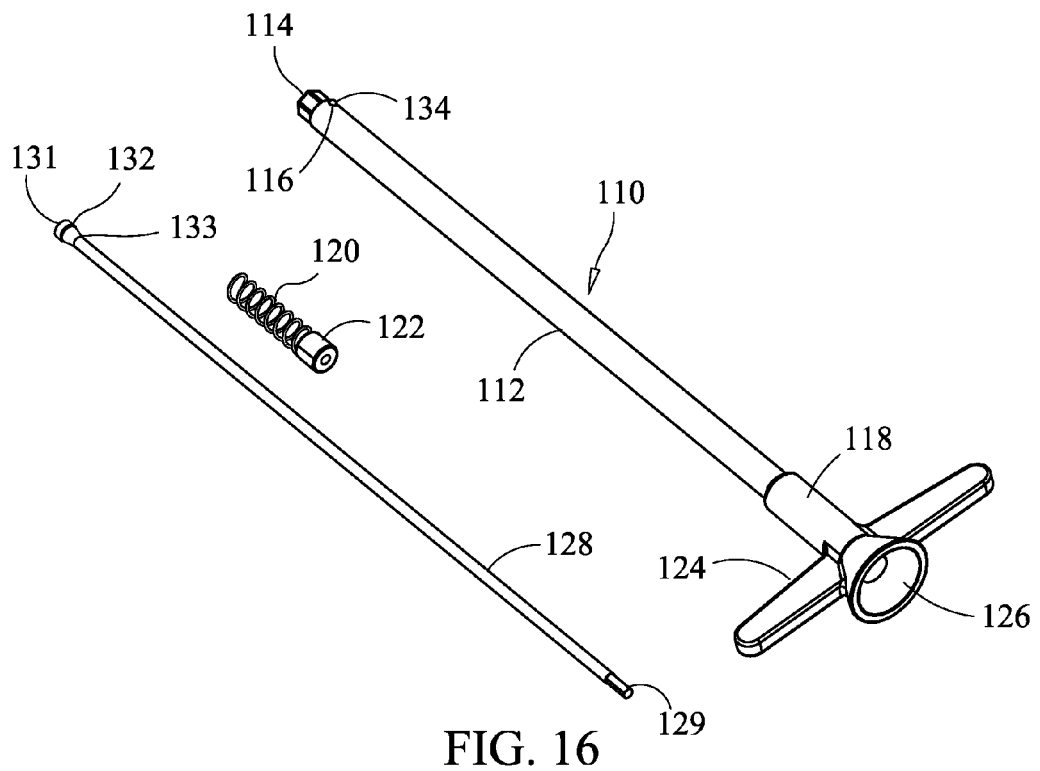
FIG. 16 is an exploded view of one of the final tools shown in FIG. 17.
Figure 17:
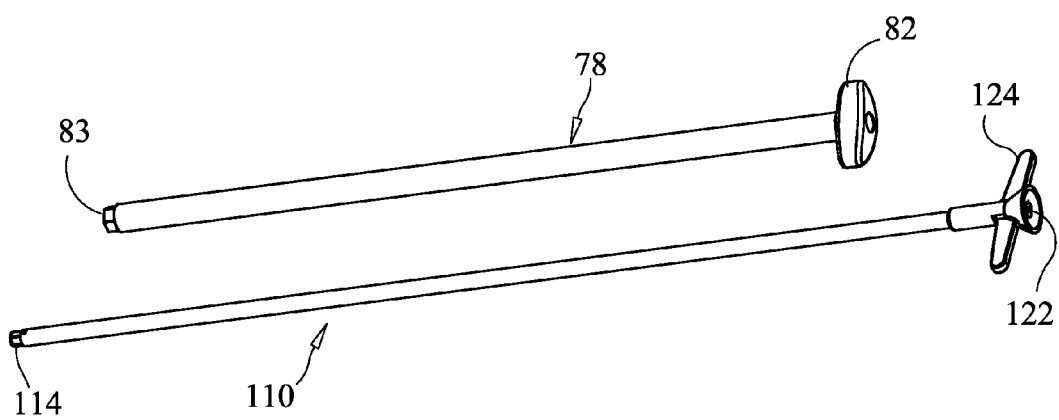
FIG. 17 is a perspective view of two final tools.

Next, a second tool assembly (final tools) is prepared whose function is to detach the distal head or disc 22 and remove the main prosthesis body 12. The assembly consists of the hex tool 78 and an engagement tool 110 as shown in FIGS. 16 and 17. Engagement tool 110 and removal hex tool 78 are shown in perspective in FIG. 17. The engagement tool 110 is shown in exploded view in FIG. 16 and consists of an open elongated tube 112 having a hex end 114, an opening 116 in the tube wall slightly axially spaced from the hex end, an enlarged section 118 near it other end to accommodate a spring 120 and push button 122, a handle 124 and a cup terminus 126 within which the push button 122 sits. A ball shaft 128 fits in the tube 112 in freely sliding fashion with one end 129 engaged with the push button 122, and the other end 131 of the ball shaft 128 having an enlarged section 132 that joins with the normal section of the ball shaft 128 by a transition section 133 that tapers. A ball 134 sits on the ball shaft 128 and is aligned with the hole or opening 116 so that it can project out the hole. In the at rest position, the tool 110 assembled as shown in FIG. 17, the push button 122 is normally being urged outwardly by spring 120 and therefore, the ball 134 is positioned on the upper portion of the tapered transition 133 so that the ball 134 projects its maximum extent possible out of the opening 116. By pushing button 122 inwardly, the ball shaft 128 is shifted so that the ball 134 will ride down the tapered section 133 to the normal section of the ball shaft 128 and therefore, the ball 134 will be retracted its maximum extent into the opening 116.

The engagement tool 110 is inserted into the hex tool 78 and the assembly is placed down the tube retractor 52 with the hex shape 83 inserted into the hex opening 28 on the implant 10. The engagement tool extends completely through the main prosthesis body 12 to the far end of the distal head 22 and the hex end 114 is received in the hex opening 24 of cap 22. During insertion, the push button 122 is depressed so that the ball 134 is retracted. When in position, the button 122 is released and ball 134 projects and engages the wall of the hex opening 24 of the cap 22. The engagement tool 110 is engaged and held with the right hand by the surgeon. The surgeon then holds the hex tool 78 with the left hand and unscrews counter-clockwise (rotates in the appropriate sense to unscrew the distal cap 22 from the main prosthesis body 12) while resisting with the right hand on the engagement tool 110 (alternatively the tool 110 can be turned clockwise while resisting with the tool 78) until cap or head 22 is fully unscrewed. The tool 110 is disengaged momentarily to let the distal head 22 release/drop off. The tool 110 is reengaged within the remainder of the prosthesis which is pulled out the rest of the way. The detachment and pull out of the prosthesis is managed quickly and easily.

Figure 14:
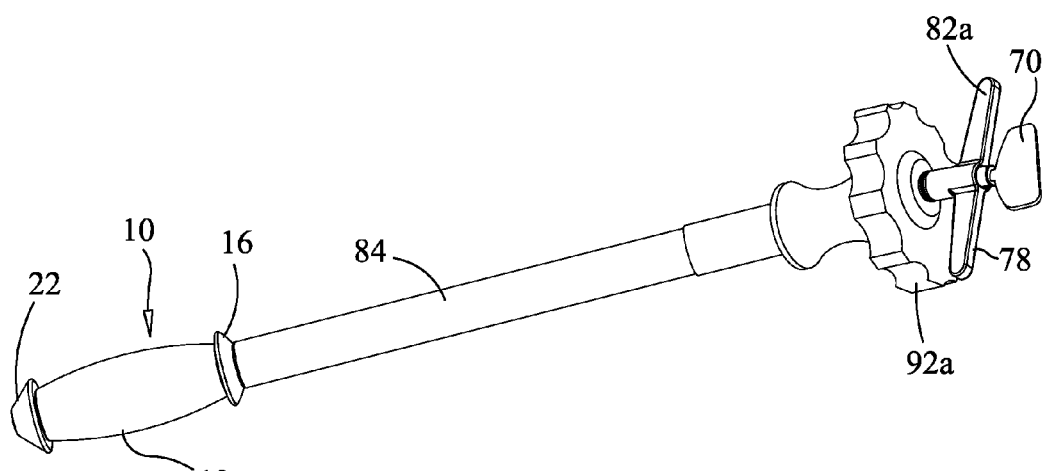
FIG. 14 is a perspective view showing a second type removal tool attached to the third embodiment of the prosthesis.

FIG. 14 shows a second embodiment of a removal tool for removing the hex locking member 30. The function is identical to the first embodiment shown in FIG. 10. The main difference lies in the use of a different designed knob 92a that has threads on its inner periphery that mate with threads on the exterior surface of the hex tool 78 and a different designed handle 82a. The depending tube 94 is eliminated and the threading on the interior surface of the sheath 84 has been eliminated. The action is between the threads on the exterior of the hex tool 78 and the knob 92a. To explant, the tube retractor goes in place against head of implant as previously described. The assembled tool consisting of the handhold sheath 84, the hex tool 78 with hex end 83, knob 92a, washer (not shown, but located between knob 92a and the end of sheath 84) and the removal tool 70 are preassembled. The preassembled tool assembly is placed down the tube retractor and engaged into the hex opening 28 on the implant 10. The removal tool 70 is screwed into hex locking member 30 as described, by turning in an appropriate sense, e.g. clockwise. Left hand holds sheath 84, handhold piece, while right hand screws knob 92a clockwise. Threads on outside of hex tool 78 are engaged by knob 92a, thus forcing the inner hex tool 78 and removal tool 70 and locking piece outward, disengaging locking piece from the distal head of the implant. The whole assembly can now be pulled all the way out.

Figure 15:
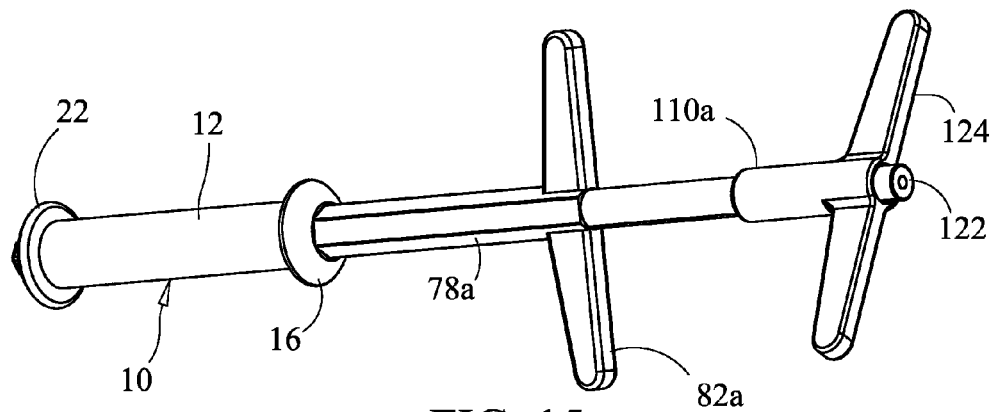
FIGS. 15 and 15a show a perspective view showing a type of final removal tools, and an exploded view, respectively, including the second embodiment of the prosthesis.
Figure 15A:
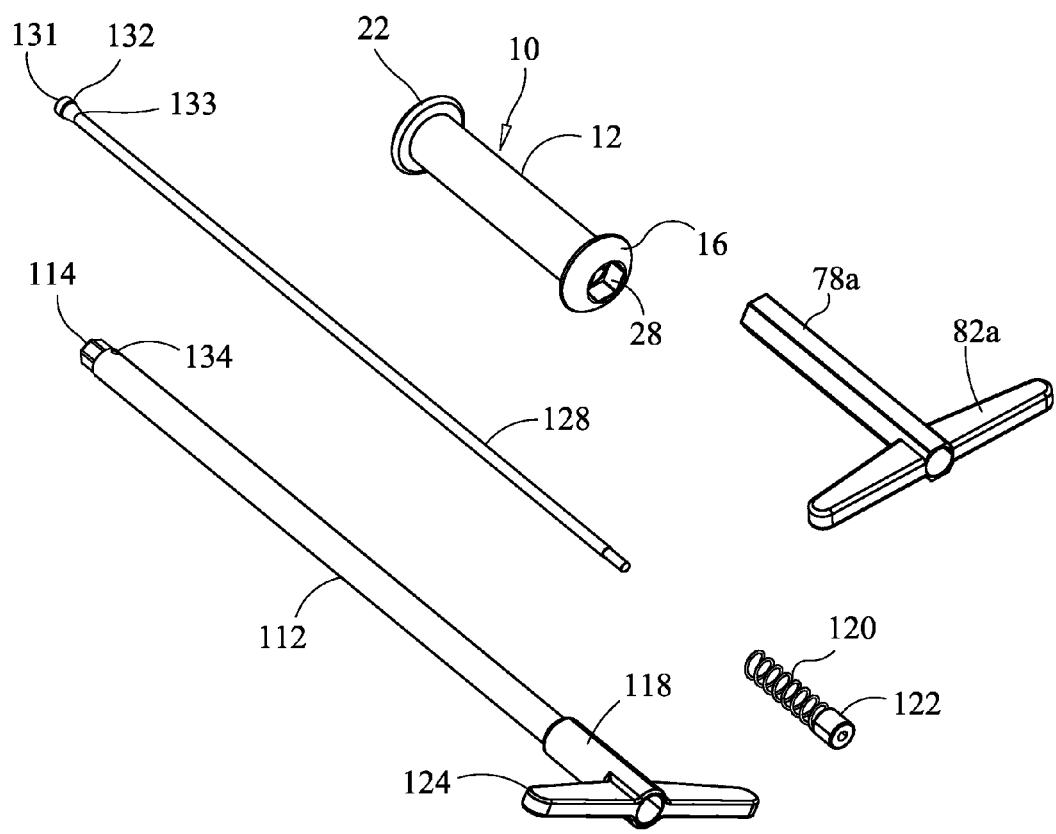

In FIGS. 15 and 15a another embodiment of the final tools shown in FIGS. 16 and 17 for detaching the cap 22 and pulling out the prosthesis is shown. The engagement tool 110a is different only in respect to the design of the terminal end as the cup 126 has been removed, and in respect to the hex tool 78, which has been shortened to tube 78a and the configuration of wing handle 82a. In all other respects the parts and function are identical.

Figure 22:
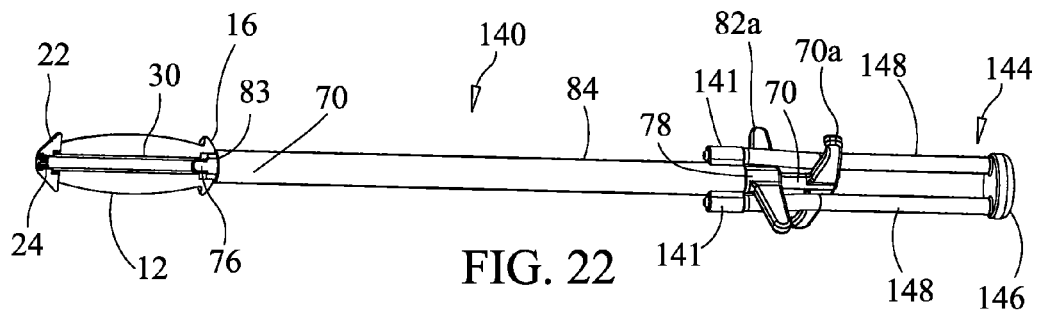
FIG. 22 is a perspective view of a fourth type of removal tool, attached to the third embodiment of the prosthesis.
Figure 23:
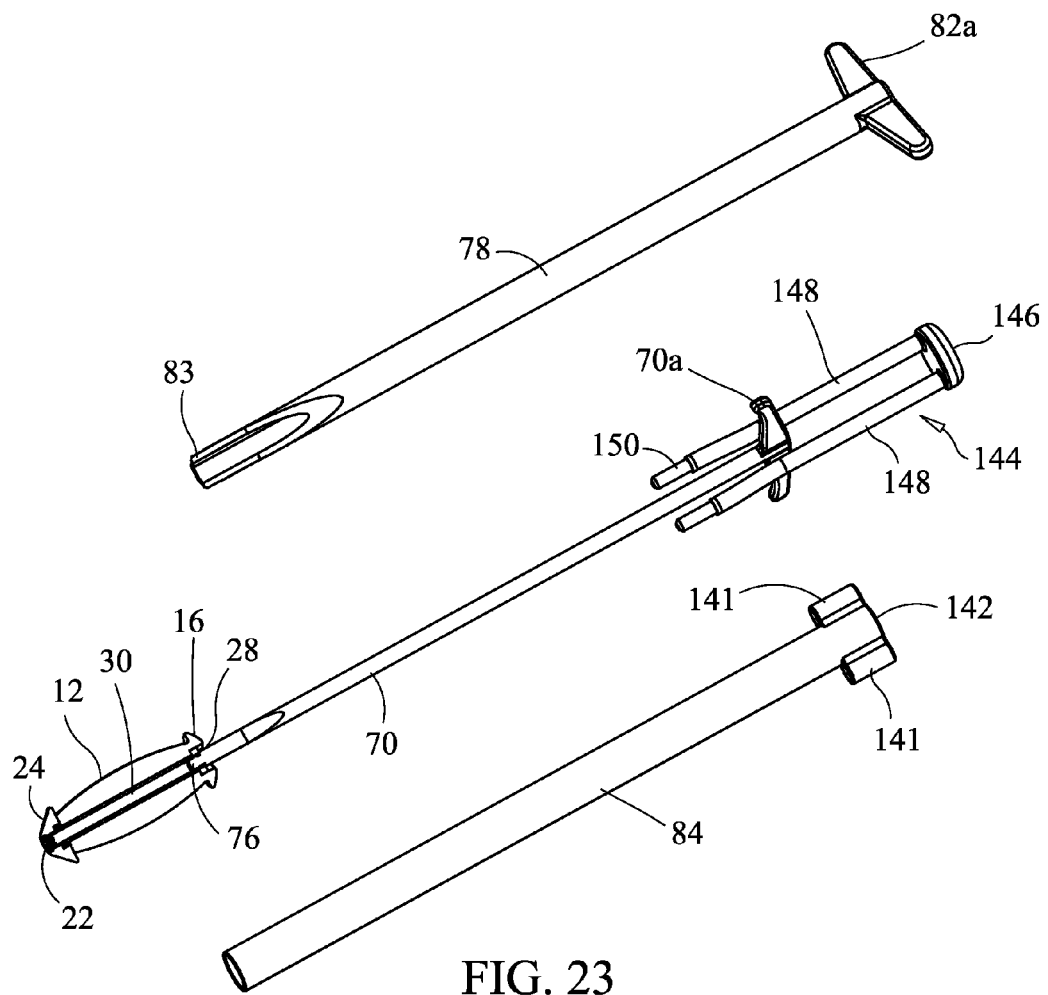
FIG. 23 is an exploded view of the fourth type of removal tool, attached to the third embodiment of the prosthesis.

FIGS. 22 and 23 show a still further embodiment of a tool assembly 140 serving the function of extracting the hex locking member 30. The components of the tool assembly 140 consist of a removal tool 78 with a hex end 83, a lock removal tool 70 with the screw thread 76 for engaging the hex locking member 30 for withdrawal, a lock removal sheath 84 provided with two small tubes 141 diametrically axially fixed to sheath 84 at its end 142, and a sheath cap 144 having a solid cap head 146 with two depending rods 148 that have reduced sections 150 at their free ends to fit into the tubes 141. Assembly of the components consists of placing tube 70 in tube 78 and placing both in sheath 84. The sheath cap is mounted to the end 142 by placing the reduced sections 150 into the tubes 141. The tube retractor goes in place against head of implant as previously described. The preassembled tool 140 is placed down the tube retractor and engaged into the hex opening 28 on the implant 10, shown here with a prolate spheroid shape for the main prosthesis body 12. The tool 70 is screwed into the inner threading of the hex locking member 30. The surgeon hold the sheath 84 with the left hand while the right hand fingers grasp the handle wings 70a, 82a of the tool 70 and the tube 78, respectively. By pushing the sheath cap 144 into palm of the right hand while pulling the tools 70 and 78, the tools 70 and 78 will be forced outwardly carrying the hex locking member 30 with them and thus, disengaging the hex locking member 30 from the hex opening 24 of the distal head or cap 22. Now the hex locking member 30 can be fully withdrawn together with the tool 140. The disengagement of the distal cap or head 22 from the main prosthesis body 12 is then conducted using final tools and in the manner previously described.

Figure 24:
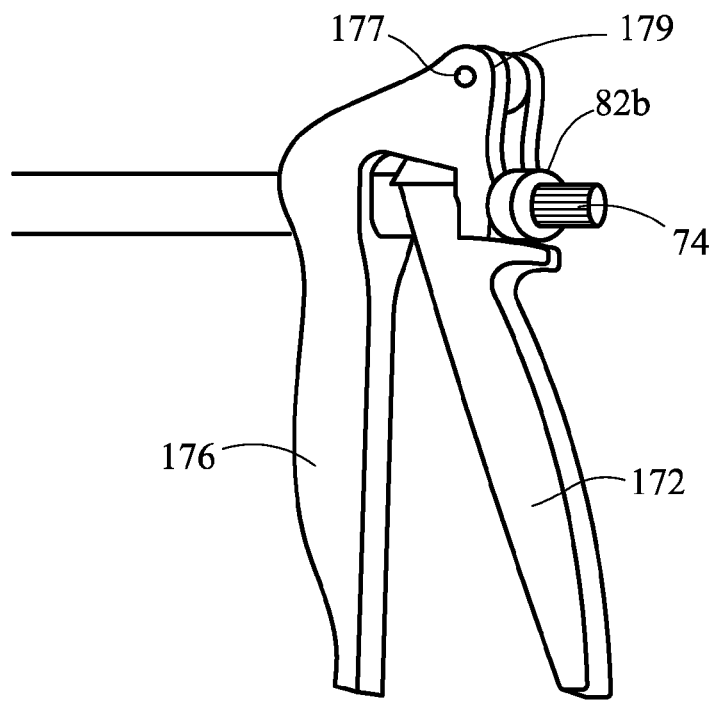
FIG. 24 is a perspective view of a pistol grip actuator for a removal tool.
Figure 25:
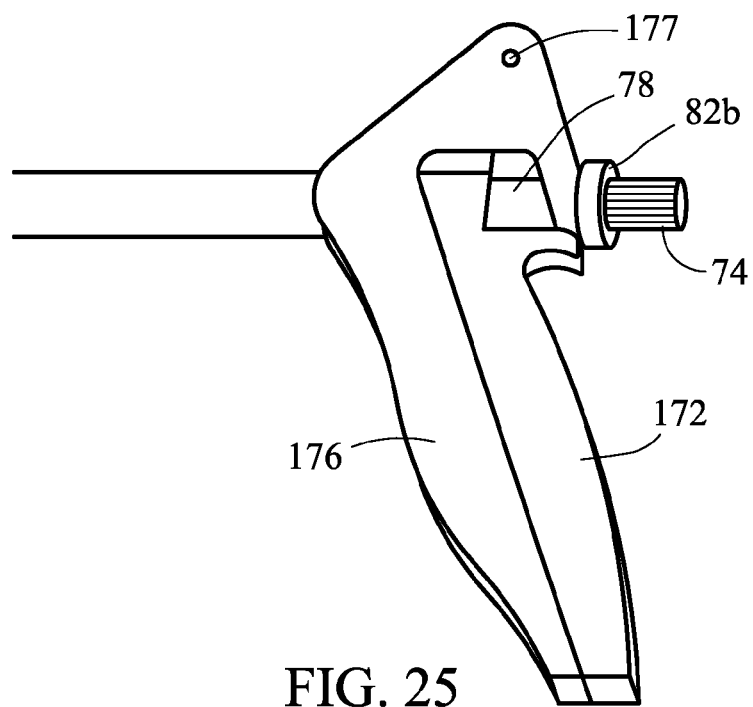
FIG. 25 is a perspective view showing the pistol grip actuator of FIG. 24 actuated.
Figure 26:
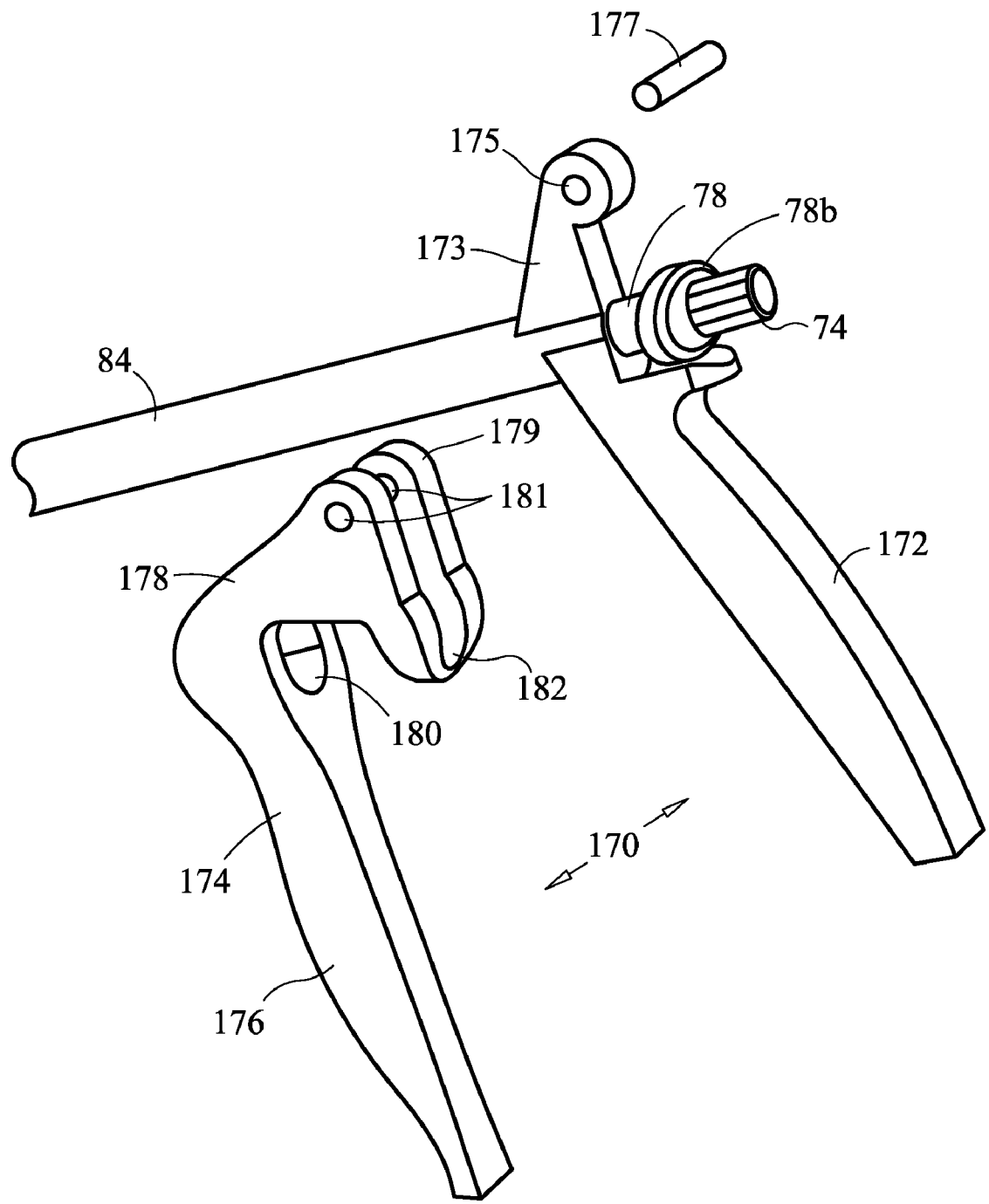
FIG. 26 is an exploded view of the pistol grip actuator.

FIGS. 24, 25 and 26 show a modified way to pull the removal hex tool 78 and lock removal tool 70 relative to the sheath 84 to withdraw the hex locking member 30. A pistol grip 170 is provided having one grip portion 172 fixed to sheath 84 with an upward extension 173 having a hole 175 to receive a pivot pin 177. The other pistol grip 174 consisting of a grip portion 176 and a bifurcated connecting portion 178 defining two saddles 180 and 182. Saddle 180 slidingly contacts with the sheath 84; saddle 182 contacts with the removal hex tool 78 and bears on head 82b. The top portion 179 of the bifurcated connecting portion 178 has holes 181. Extension 173 fits between the two parts of the bifurcation and holes 175 and 181 are aligned and a pivot pin 177 pivotally interconnects the two grip portions. FIG. 24 shows the at rest position of the pistol grip, and FIG. 25 shows the actuated position where it can be seen that the heads of the tools 78 and 70 have been moved in a withdrawal sense or direction to withdraw the hex locking member 30 from the hex opening 24 of the distal head or cap 22.

Figure 27:
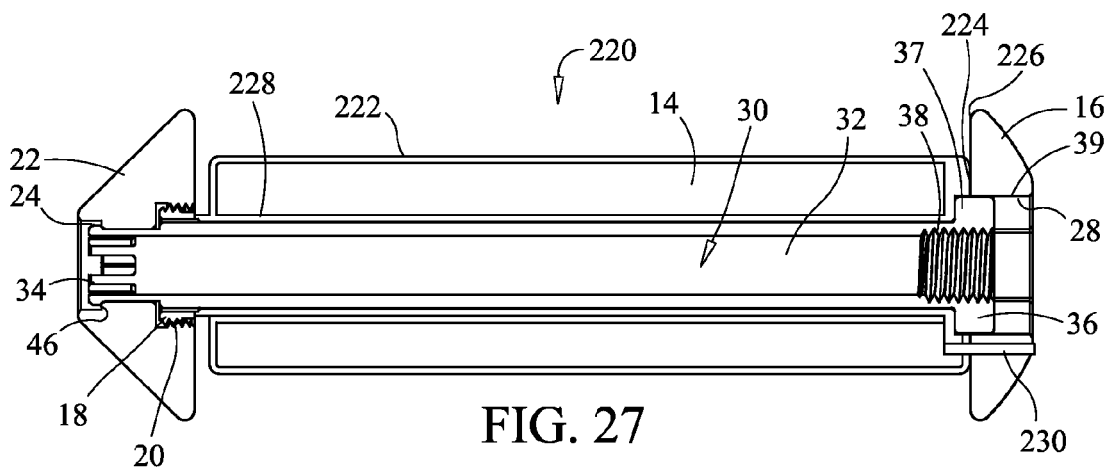
FIG. 27 is a sectional view along the longitudinal axis of an implant according to the present invention that is either fillable by a fluid or inflatable by a gas.
Figure 28A:
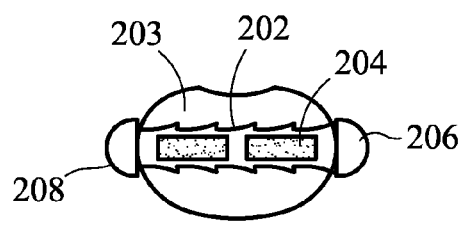
FIGS. 28 (a) to (e) show schematically a prosthesis for fusion of abutting vertebrae as (a) a cross-section of a prosthesis having a cage, in place in a disc, with a bone graft/BMP material loaded into the cage and exposed top and bottom to contact abutting vertebrae; (b) a front view of the prosthesis; (c) a cutaway coronal view of the prosthesis showing the cage in place in a damaged disc; (d) a perspective view of the cage with the bone graft/BMP material exposed; and (e) a lateral view of abutting vertebrae with the prosthesis in place.
Figure 28D:
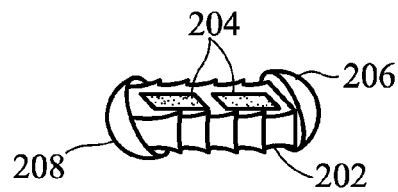
Figure 28B:
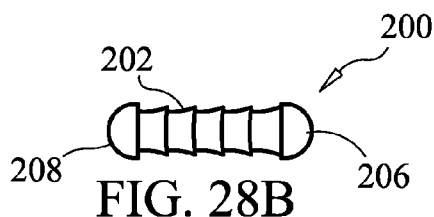
Figure 28C:
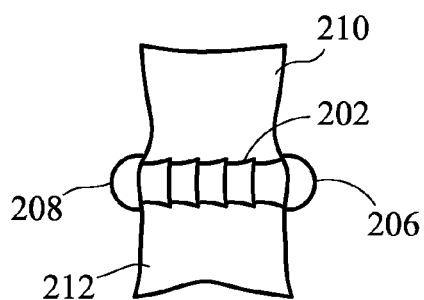
Figure 28E:
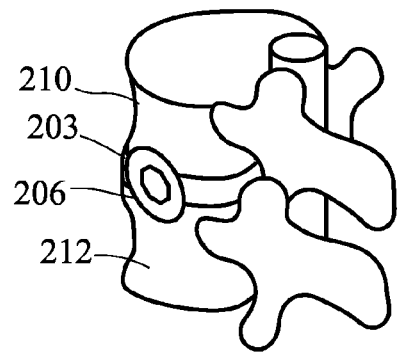

The prosthesis of the present invention can be made of surgical steel, other types of metal, plastic, rubber, polymer (especially PEEK and acrylic polymers) and ceramic and combinations of these materials. The main prosthesis body 12 can be hollow and/or inflatable and filled with water, air, hydrogel silicone rubber, acrylic, other liquid or gas under pressure, as shown in FIG. 27. In this construction, the main prosthesis body is annular having an outer portion 222 of the main prosthesis body 220 that a flexible or resilient layer or covering 222 that is attached at 224 to the inside surface 226 of the disc 16 and to the outer surface of the central inner annular tube 228. A one-way valve 230 is provided for filling or inflating. The profile of the filled or inflated annular main prosthesis lies within the profile of the distal and proximal heads 22 and 16, respectively, so that the prosthesis can be forced into the hole drilled in the disc. The filling or inflation can be done after the prosthesis has been forced through the hole or before. In any event, when in place, the filled or inflated prosthesis distracts the abutting vertebrae slightly and the two heads bear against the abutting vertebrae, but in a manner to allow or enable the distal head 22 to be rotated relative to the main prosthesis body when it is desired to remove the prosthesis.

Whereas the coupling of the disc 22 and the main prosthesis body 12 is shown by threading, other types of coupling can be used. For example, this coupling can be a bayonet type coupling for quick easy connection and decoupling. For a bayonet coupling, it is only necessary to relatively rotate the coupled parts by as little as 30 to 45 degrees.

The cross sectional shape of the body 12 can be racetrack shape with straight sides.

The implantation technique can be used also for spinal fusion, as shown by the views of FIGS. 28 (a) to (e). For example, if the body 202 of the implant 200 were a hollow cage in the shape of a rectangular prism, filled with bone and BMP (bone morphogenic protein) 204 for example, it could be used as a spinal fusion device and placed into a hole drilled in the disc 203 as previously described, the disc being between abutting vertebrae 210, 212. It would have advantages over existing cages because it would be effectively anchored into place by the two heads 206 and 208 (to prevent lateral displacement) and the remaining disc annulus (to prevent posterior-anterior displacement), without screwing anything into the vertebrae.

Implant 200, like the other prosthesis of the present invention can be made of any suitable biocompatible material. In this regard, the present invention envisions making any of the prosthesis of a hydrophilic material. Such materials swell to a predetermined shape when exposed to liquid, such as body fluid. A hydrophilic implant could further facilitate implantation since the implant would expand to the final desired shape in vivo.

Although the invention has been shown and described in terms of specific embodiments, changes and modifications can be made by those skilled in the art, which do not depart from the teachings herein. Such changes and modifications are deemed to fall within the purview of the appended claims.

What is claimed is:

1. A spinal prosthesis for inserting laterally from one side only into an intervertebral disc space between two adjacent vertebrae comprising:
    an elongated, rigid load-bearing main prosthesis body having opposed ends and having a vertical height deliberately greater than the height of normal disc space of an intervertebral disc into which it is to be inserted and having opposed elongated surfaces configured to contact and distract the upper and lower adjacent vertebrae, said main prosthesis body sized to fit laterally from one side of a disc to the other at its mid-plane and sized to maintain the space between the adjacent vertebrae distracted;
    a first cap directly mounted in fixed relation on one end of the main prosthesis body in a position to lie outside the normal disc space of an intervertebral disc and sized to have a vertical height greater than the vertical height of the main prosthesis body to bear against the sides of the adjacent vertebrae; and
    a second cap removably mounted on the other end of the main prosthesis body in a position to lie outside the normal disc space of an intervertebral disc and sized to have a vertical height greater than the vertical height of the main prosthesis body to bear against the sides of the adjacent vertebrae.

2. A prosthesis according to claim 1 wherein said second cap and said main prosthesis body mutually define coacting elements to prevent relative longitudinal movement.

3. A prosthesis according to claim 1 further including an elongated locking member received in the main prosthesis body and directly contacting both caps to prevent relative rotary movement of said second cap and the main prosthesis body.

4. A spinal prosthesis for inserting laterally from one side only into an intervertebral disc space between two adjacent vertebrae comprising:
    an elongated, rigid, load-bearing, tubular main prosthesis body having opposed ends and having a vertical height deliberately greater than the height of normal disc space of an intervertebral disc into which it is to be inserted and having opposed elongated surfaces configured to contact and distract the upper and lower adjacent vertebrae, said main prosthesis body sized to fit laterally from one side of a disc to the other at its mid-plane and sized with a vertical height to maintain the space between the adjacent vertebrae distracted, said main prosthesis body having a longitudinally extending through passageway open at its ends;
    a proximal cap directly attached to one end of the main prosthesis body in a position to lie outside the normal disc space of an intervertebral disc and sized to have a vertical height greater than the vertical height of the main prosthesis body to bear against the sides of the adjacent vertebrae and defining an opening in axial alignment with one end of said passageway;
    a distal cap directly detachably attached to the other end of the main prosthesis body in a position to lie outside the normal disc space of an intervertebral disc and sized to have and having a vertical height greater than the vertical height of the main prosthesis body to bear against the sides of the adjacent vertebrae and defining an opening in axial alignment with the other end of said passageway; and
    an elongated, locking member received in said passageway and having a first end engaging the opening in said proximal cap and a second end engaging the opening of said distal cap to prevent relative movement.

5. The prosthesis according to claim 4, wherein said main prosthesis body is cylindrical in shape.

6. The prosthesis according to claim 5, wherein main prosthesis body is one of right cylindrical, elliptical and prolate spheroid shape.

7. The prosthesis according to claim 4, wherein said main prosthesis body is made from a material selected from the group consisting of metal, a synthetic polymer, rubber, ceramic, PEEK, acrylic, and combinations thereof.

8. The prosthesis according to claim 4, wherein said caps are disc shaped.

9. The prosthesis according to claim 4, wherein said distal cap is attached to the main prosthesis body by a joint that requires relative rotation to detach.

10. The prosthesis according to claim 4, wherein the openings in said caps are non-circular shaped.

11. The prosthesis according to claim 10, wherein the opening in said distal cap is hex shaped.

12. The prosthesis according to claim 10, wherein said locking member has a non-circular shaped end that is received in the non-circular shaped opening in the distal cap.

13. The prosthesis according to claim 12, wherein the locking member and the distal cap mutually define quick detachable mutually coacting elements that prevent longitudinal movement of the locking member relative to the distal cap.

14. The prosthesis according to claim 13, wherein said quick detachable mutually coacting elements comprise projecting flat bars peripherally arranged in a non-circular shape at the second end of the locking member, each bar having peripherally extending bump coacting with a shoulder defined in the non-circular shaped opening of the distal cap.

15. The prosthesis according to claim 4, wherein said caps have flat surfaces facing inwardly toward the main prosthesis body.

16. The prosthesis according to claim 4, wherein the opening in said first cap is non-circular shaped.

17. The prosthesis according to claim 16, wherein the locking member is non-circular shaped at its first end and fits into the non-circular shaped opening of the first cap in a recessed manner.

18. A method for treating a person having a damaged intervertebral disc comprising the steps of:
  i. providing a prosthesis comprised of a single integrated assembled structure including (a) an elongated, stiff main prosthesis body having opposed ends having a length to fit laterally from one side of a disc to the other at its mid-plane, said main prosthesis body having a vertical height slightly greater than the height of normal disc space of a damaged intervertebral disc into which it is implanted, and having a shape in cross section normal to its longitudinal axis so that the main prosthesis body will make contact with abutting vertebrae to the damaged intervertebral disc parallel with its longitudinal axis; (b) a proximal head directly contacting and mounted on one end of the main prosthesis body having a vertical height greater than the vertical height of the main prosthesis body; (c) a distal head directly contacting and mounted on the other end of the main prosthesis body having a vertical height greater than the vertical height of the main prosthesis body;
  ii. forming a hole laterally completely through the damaged intervertebral disc to create opening in the intervertebral disc on opposed lateral sides,
  iii. feeding the single integrated assembled prosthesis into the hole in the damaged intervertebral disc from one side only distal head first; and
  iv. then forcing the prosthesis through the hole in the damaged intervertebral disc causing the distal head to distract the adjacent abutting vertebrae until the distal head emerges from the other side of the hole at which time the heads will be on both sides of said damaged intervertebral disc bearing against the vertebrae abutting to the damaged intervertebral disc, and the main prosthesis body will still be distracting the adjacent abutting vertebrae.

19. A method of explanting a prosthesis implanted according to claim 18 including the further steps of:
  e. engaging the implanted prosthesis from a proximal side;
  f. detaching the distal head of the prosthesis from the proximal side; and
  g. removing the remaining portion of the implanted prosthesis from the proximal side.

20. A method for treating a person having a damaged intervertebral disc comprising the steps of:
  i. providing a prosthesis comprised of a single integrated assembled structure including (a) an elongated, stiff, tubular main prosthesis body having opposed ends, having a longitudinally extending through passageway open at its ends and having a length to fit laterally from one side of a disc to the other at its mid-plane, said main prosthesis body having a vertical height slightly greater than the height of normal disc space of an intervertebral disc into which it will be inserted, and having a shape in cross section normal to its longitudinal axis so that main prosthesis body, when inserted, will contact with abutting vertebrae to the intervertebral disc parallel with its longitudinal axis; (b) a proximal head directly contacting and attached to one end of the main prosthesis body having a vertical height greater than the vertical height of the main prosthesis body and defining an opening in axial alignment with one end of said passageway; (c) a distal head directly contacting and detachably attached to the other end of the main prosthesis body having a vertical height greater than the vertical height of the main prosthesis body and defining an opening in axial alignment with the other end of said passageway and (d) an elongated locking member received in said passageway having a first end directly contacting and engaging the opening in said proximal head and a second end directly contacting and engaging the opening of said distal head to prevent relative movement;
  ii. forming a hole laterally completely through the damaged intervertebral disc to create openings on opposed lateral sides of the damaged intervertebral disc,
  iii. feeding the single integrated assembled prosthesis into the hole in the damaged intervertebral disc from one side only distal head first; and
  iv. then forcing the prosthesis through the hole in the damaged intervertebral disc causing the distal head to distract the adjacent abutting vertebrae until the distal head emerges from the other side of the hole at which time the heads will be on both sides of said damaged intervertebral disc bearing against vertebrae abutting to the damaged intervertebral disc, and the main prosthesis body will still be distracting the adjacent abutting vertebrae.

21. A method of explanting a prosthesis implanted according to claim 20 including the further steps of:
  e. engaging the implanted prosthesis from a proximal side;
  f. unlocking and removing the locking member from the proximal side;
  g. detaching the distal head of the prosthesis from the proximal side; and
  h. removing the unlocked remaining portion of the implanted prosthesis from the proximal side.

22. A method for treating a person having a damaged intervertebral disc between abutting vertebrae comprising the steps of:
  a. providing a prosthesis comprised of a single integrated assembled structure including (i) an elongated, stiff main prosthesis body having opposed ends, having a length to fit laterally from one side of a disc to the other, said main prosthesis body having a vertical height slightly greater than the height of normal disc space of an intervertebral disc into which it will be inserted, and having a shape in cross section normal to its longitudinal axis so that main prosthesis body, when inserted, will contact with abutting vertebrae to the intervertebral disc parallel with its longitudinal axis, said body containing one of bone and a material exposed to grow bone to or from vertebral surfaces; (ii) a proximal and distal head directly contacting and attached to opposite ends of the main prosthesis body having a vertical height greater than the vertical height of the main prosthesis body;
  b. forming a hole laterally completely through the damaged intervertebral disc to create openings on opposed lateral sides of the damaged intervertebral disc,
  c. feeding the single integrated assembled prosthesis into the hole in the damaged intervertebral disc from one side only, distal head first; and
  d. then forcing the prosthesis through the hole in the damaged intervertebral disc so that the heads project out of said openings on both sides of said damaged intervertebral disc; wherein the main prosthesis body lies between the abutting vertebrae distracting them slightly so that the said one of exposed bone and material contacts the surfaces of the abutting vertebrae and the projecting heads bear against the abutting vertebrae.

23. A method for treating a person having a damaged intervertebral disc comprising the steps of:

a. providing a prosthesis comprised of a single integrated assembled structure including (i) an elongated, stiff, tubular main prosthesis body having opposed ends and having a length to fit laterally from one side of a disc to the other at its mid-plane, said main prosthesis body having a vertical height slightly greater than the height of normal disc space of a damaged intervertebral disc into which it will be implanted, and having a shape in cross section normal to its longitudinal axis so that main prosthesis body makes contact with abutting vertebrae to the damaged intervertebral disc parallel with its longitudinal axis, and the main prosthesis body having an inner, hollow, stiff, annular configuration with an outer covering being fillable by a fluid, (ii) a proximal head mounted on one end of the main prosthesis body having a vertical height greater than the vertical height of the main prosthesis body, (iii) a distal head mounted on the other end of the main prosthesis body having a vertical height greater than the vertical height of the main prosthesis body;

b. forming a hole laterally completely through the damaged intervertebral disc to create opening in the intervertebral disc on opposed lateral sides, c. feeding the prosthesis into the hole in the damaged intervertebral disc from one side only, distal head first; and d. then forcing the prosthesis through the hole in the damaged intervertebral disc so that the heads project out of said openings on both sides of said damaged intervertebral disc; wherein the projecting heads bear against the vertebrae abutting to the damaged intervertebral disc and e. feeding fluid into the covering to inflate.

* * * * *